United States Patent
Nguyen et al.

(10) Patent No.: US 8,790,387 B2
(45) Date of Patent: Jul. 29, 2014

(54) EXPANDABLE SHEATH FOR INTRODUCING AN ENDOVASCULAR DELIVERY DEVICE INTO A BODY

(75) Inventors: Duy Nguyen, Corona, CA (US); Kim Nguyen, Irvine, CA (US); Thanh V. Nguyen, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 11 days.

(21) Appl. No.: 13/312,739

(22) Filed: Dec. 6, 2011

(65) Prior Publication Data

US 2012/0083877 A1    Apr. 5, 2012

Related U.S. Application Data

(63) Continuation-in-part of application No. 12/249,867, filed on Oct. 10, 2008, now Pat. No. 8,690,936.

(51) Int. Cl.
*A61F 2/06* (2013.01)
*A61F 2/24* (2006.01)
*A61B 19/00* (2006.01)

(52) U.S. Cl.
CPC ............. *A61F 2/2427* (2013.01); *A61F 2/2436* (2013.01); *A61F 2/2418* (2013.01); *A61B 19/54* (2013.01)
USPC ..... 623/1.11; 604/523; 604/525; 604/103.14; 604/164.03

(58) Field of Classification Search
USPC ........ 606/191, 192, 194, 198; 623/1.11, 1.12, 623/1.23, 1.26, 1.3; 604/272, 264, 103.06, 604/93.01, 523, 536, 131, 525, 103.14, 604/164.03
See application file for complete search history.

(56) References Cited

U.S. PATENT DOCUMENTS

| | | | |
|---|---|---|---|
| 4,710,181 A * | 12/1987 | Fuqua | 604/514 |
| 4,716,901 A | 1/1988 | Jackson et al. | |
| 4,738,666 A | 4/1988 | Fuqua | |
| 4,921,479 A | 5/1990 | Grayzel | |
| 5,104,388 A | 4/1992 | Quackenbush | |
| 5,158,545 A | 10/1992 | Trudell et al. | |
| 5,176,659 A | 1/1993 | Mancini | |
| 5,217,468 A | 6/1993 | Clement | |

(Continued)

FOREIGN PATENT DOCUMENTS

| | | | |
|---|---|---|---|
| EP | 0177177 A2 | 4/1986 | |
| EP | 0249456 A2 | 12/1987 | |

(Continued)

*Primary Examiner* — Darwin Erezo
*Assistant Examiner* — Katrina Stransky
(74) *Attorney, Agent, or Firm* — Klarquist Sparkman, LLP

(57) ABSTRACT

Embodiments of an expandable sheath can be used in conjunction with a catheter assembly to introduce a prosthetic device, such as a heart valve, into a patient. Such embodiments can minimize trauma to the vessel by allowing for temporary expansion of a portion of the introducer sheath to accommodate the delivery apparatus, followed by a return to the original diameter once the prosthetic device passes through. Some embodiments can include a sheath with inner and outer layers, where a folded portion of the inner layer extends through a slit in the outer layer and a portion of the outer layer overlaps the folded portion of the inner layer. Some embodiments include an elastic outer cover positioned outside the outer layer. Embodiments of the present expandable sheath can avoid the need for multiple insertions for the dilation of the vessel, thus offering advantages over prior art introducer sheaths.

19 Claims, 28 Drawing Sheets

(56) References Cited

U.S. PATENT DOCUMENTS

| | | | |
|---|---|---|---|
| 5,234,425 A | 8/1993 | Fogarty et al. | |
| 5,256,150 A | 10/1993 | Quiachon et al. | |
| 5,318,588 A | 6/1994 | Horzewski et al. | |
| 5,380,304 A | 1/1995 | Parker | |
| 5,514,091 A | 5/1996 | Yoon | |
| 5,514,236 A | 5/1996 | Avellanet et al. | |
| 5,810,776 A | 9/1998 | Bacich et al. | |
| 5,827,227 A | 10/1998 | DeLago | |
| 5,895,410 A | 4/1999 | Forber et al. | |
| 5,964,730 A | 10/1999 | Williams et al. | |
| 5,997,508 A | 12/1999 | Lunn et al. | |
| 6,090,072 A | 7/2000 | Kratoska et al. | |
| 6,090,136 A | 7/2000 | McDonald et al. | |
| 6,190,357 B1 * | 2/2001 | Ferrari et al. | 604/102.01 |
| 6,494,860 B2 | 12/2002 | Rocamora et al. | |
| 6,632,236 B2 | 10/2003 | Hogendijk | |
| 6,814,715 B2 | 11/2004 | Bonutti et al. | |
| 6,899,727 B2 | 5/2005 | Armstrong et al. | |
| 7,144,386 B2 | 12/2006 | Korkor et al. | |
| 7,329,268 B2 | 2/2008 | Van Nguyen et al. | |
| 7,534,250 B2 | 5/2009 | Schaeffer et al. | |
| 7,785,360 B2 | 8/2010 | Freitag | |
| 2002/0032459 A1 | 3/2002 | Horzewski et al. | |
| 2004/0087968 A1 | 5/2004 | Core | |
| 2005/0085842 A1 | 4/2005 | Eversull et al. | |
| 2005/0124937 A1 | 6/2005 | Kick et al. | |
| 2005/0222576 A1 | 10/2005 | Kick et al. | |
| 2006/0020321 A1 | 1/2006 | Parker | |
| 2006/0135962 A1 * | 6/2006 | Kick et al. | 606/108 |
| 2006/0135981 A1 * | 6/2006 | Lenker et al. | 606/191 |
| 2006/0217755 A1 | 9/2006 | Eversull et al. | |
| 2007/0021768 A1 | 1/2007 | Nance et al. | |
| 2007/0074805 A1 * | 4/2007 | Leeflang et al. | 156/84 |
| 2008/0114331 A1 * | 5/2008 | Holman et al. | 604/509 |
| 2008/0200943 A1 | 8/2008 | Barker et al. | |
| 2008/0243081 A1 | 10/2008 | Nance et al. | |

FOREIGN PATENT DOCUMENTS

| | | |
|---|---|---|
| EP | 0385920 A2 | 9/1990 |
| WO | 9219312 A1 | 11/1992 |
| WO | 9307812 A1 | 4/1993 |
| WO | 2003002181 A2 | 1/2003 |
| WO | 2004002562 A2 | 1/2004 |
| WO | 2005018728 A2 | 3/2005 |
| WO | 2007035471 A2 | 3/2007 |
| WO | 2008002915 A2 | 1/2008 |
| WO | 2008042311 A1 | 4/2008 |

* cited by examiner

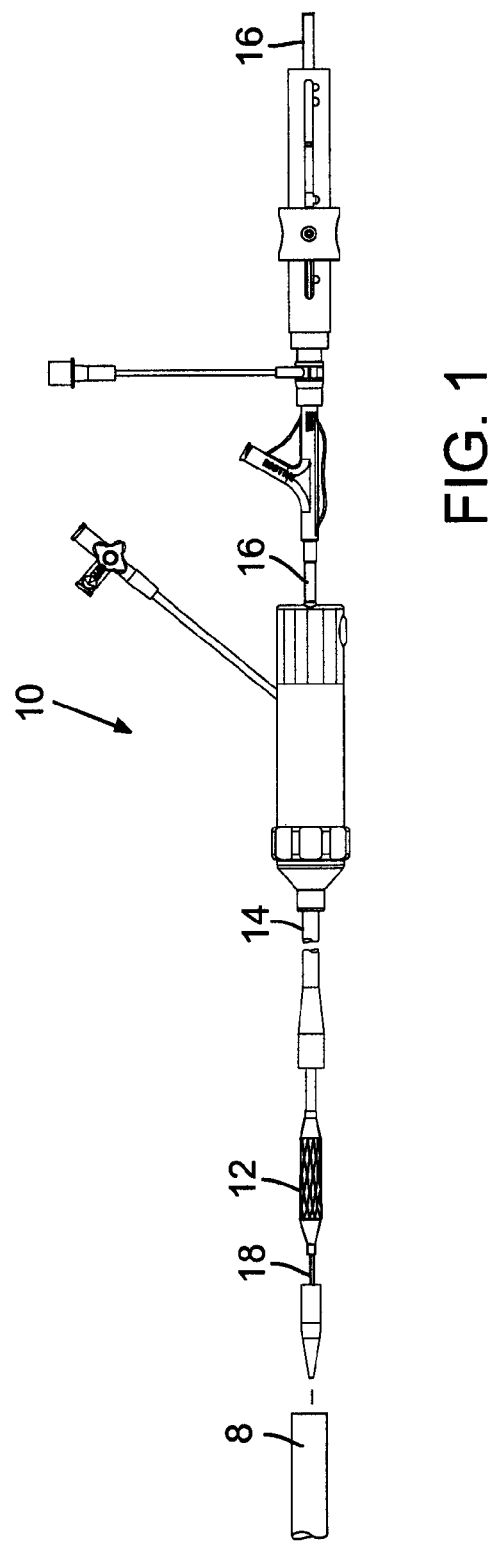

FIG. 32F
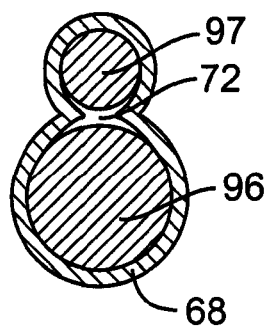
FIG. 32G
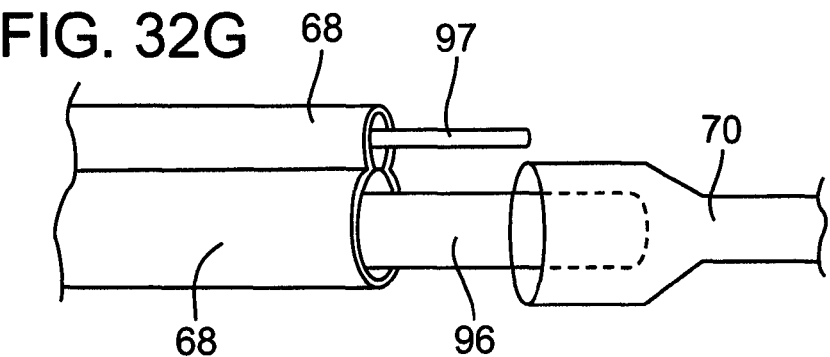
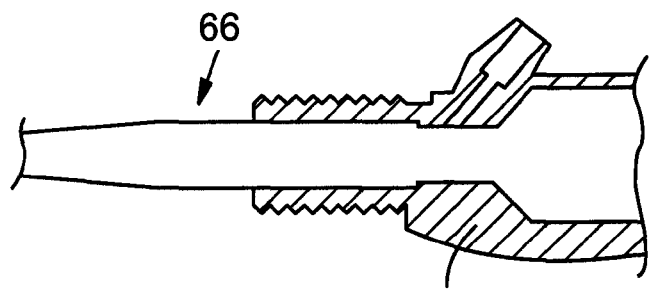
FIG. 32H

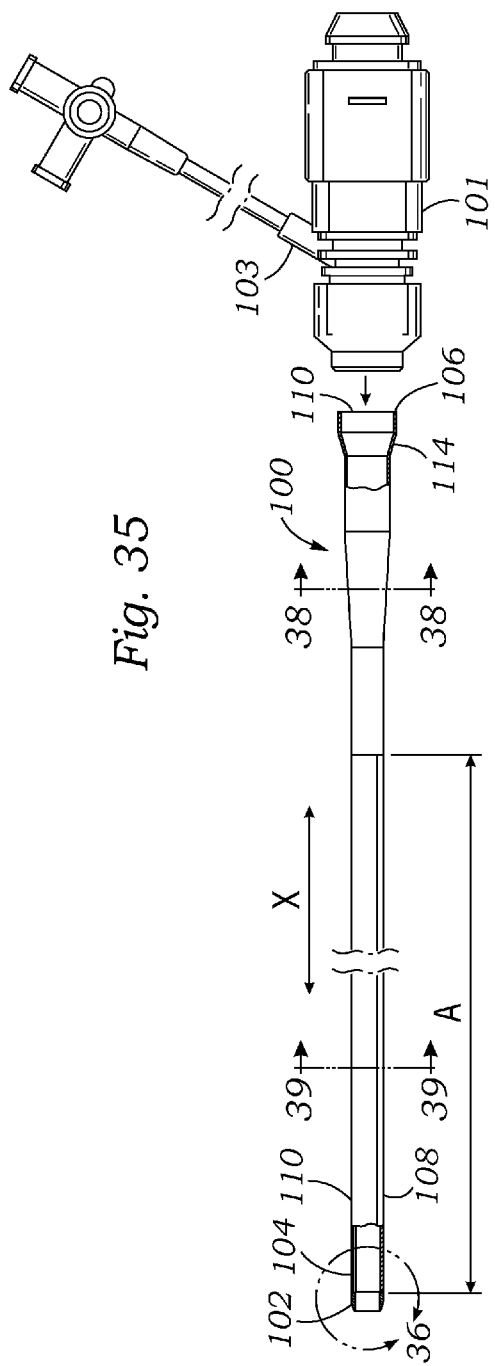
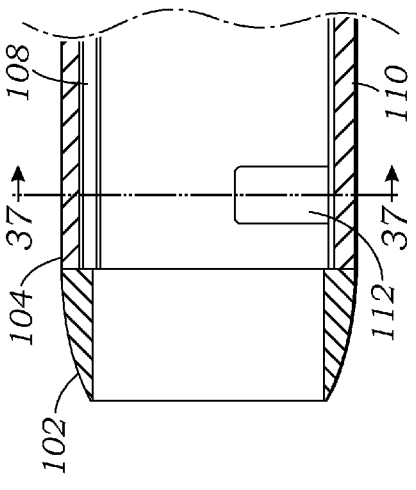
Fig. 35
Fig. 36

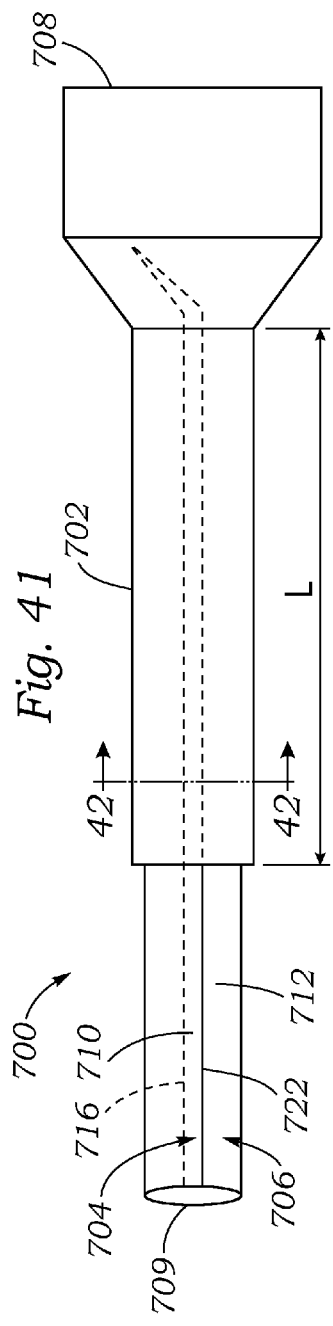
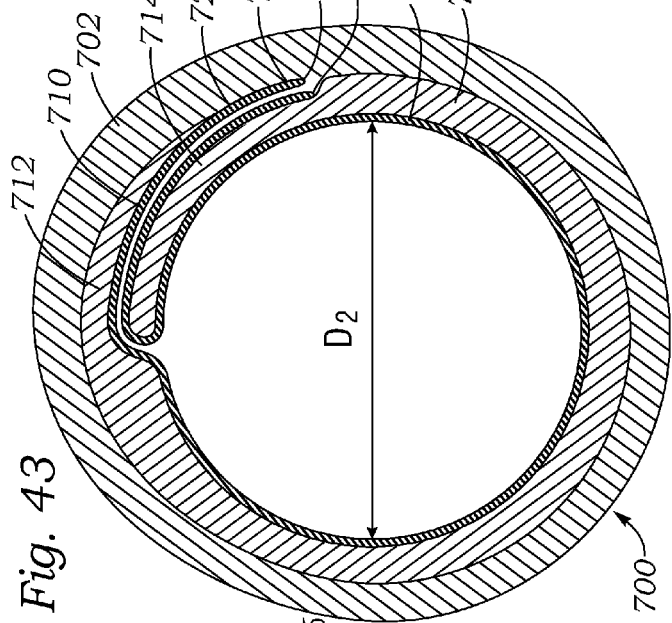
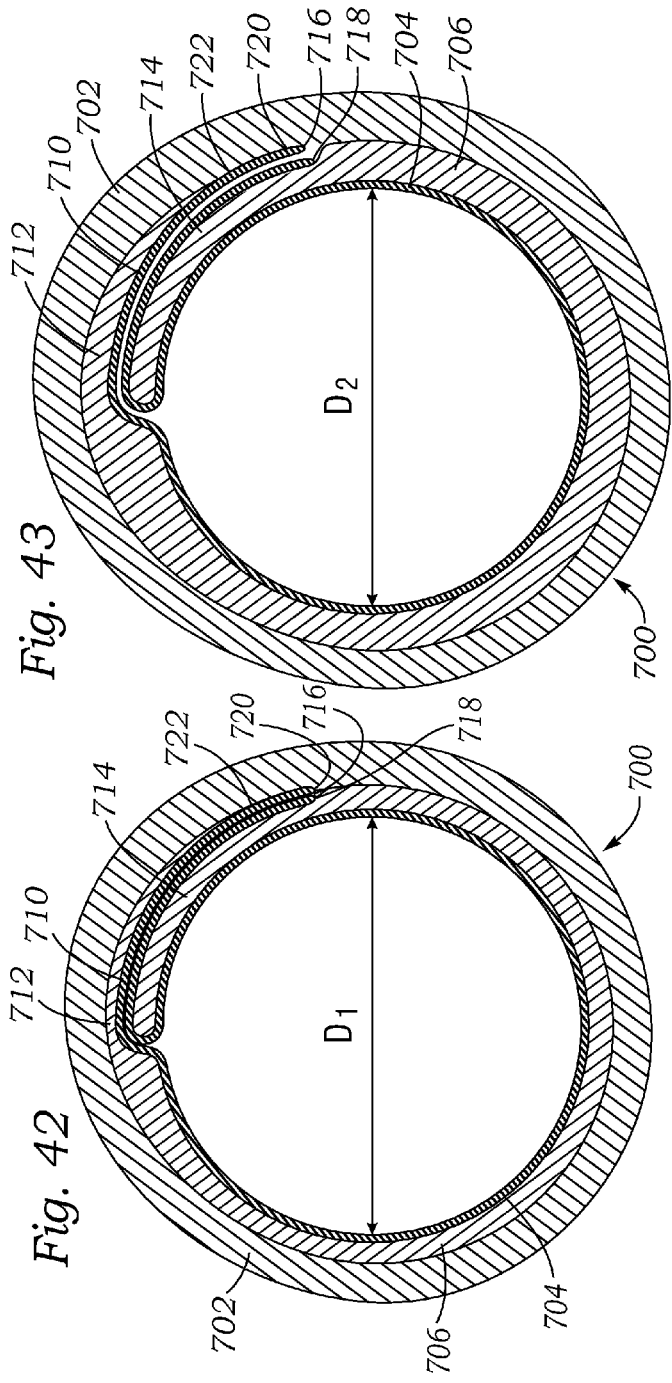

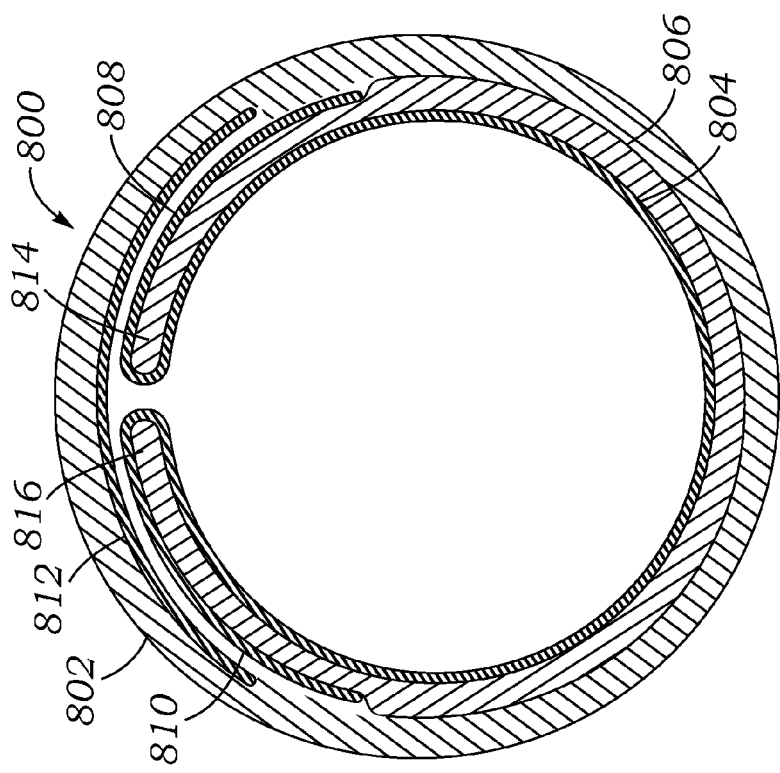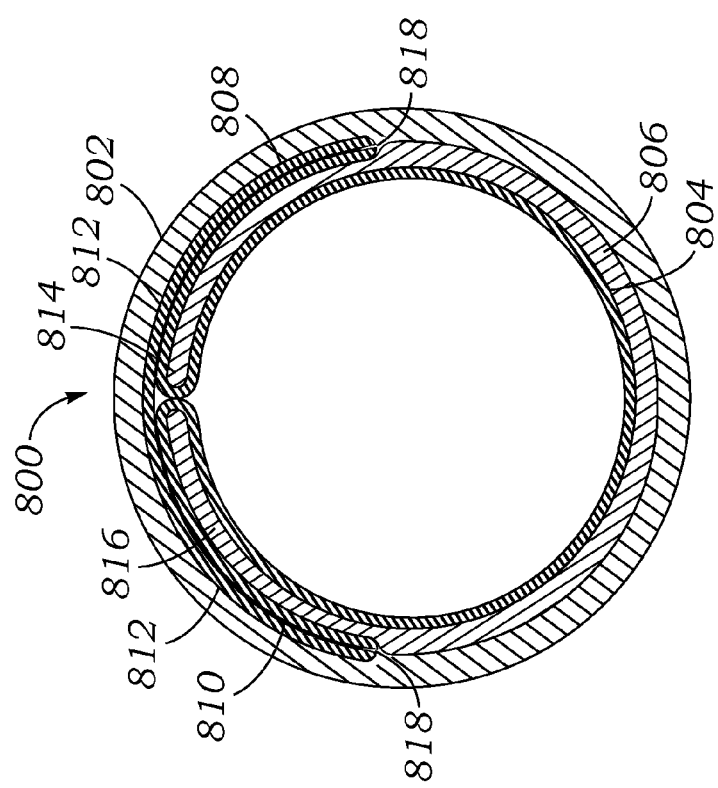

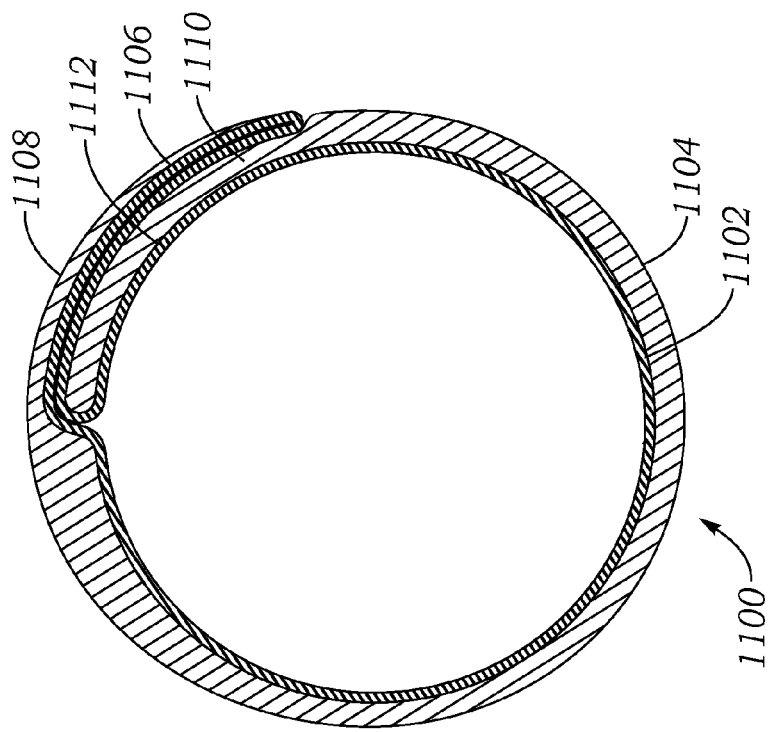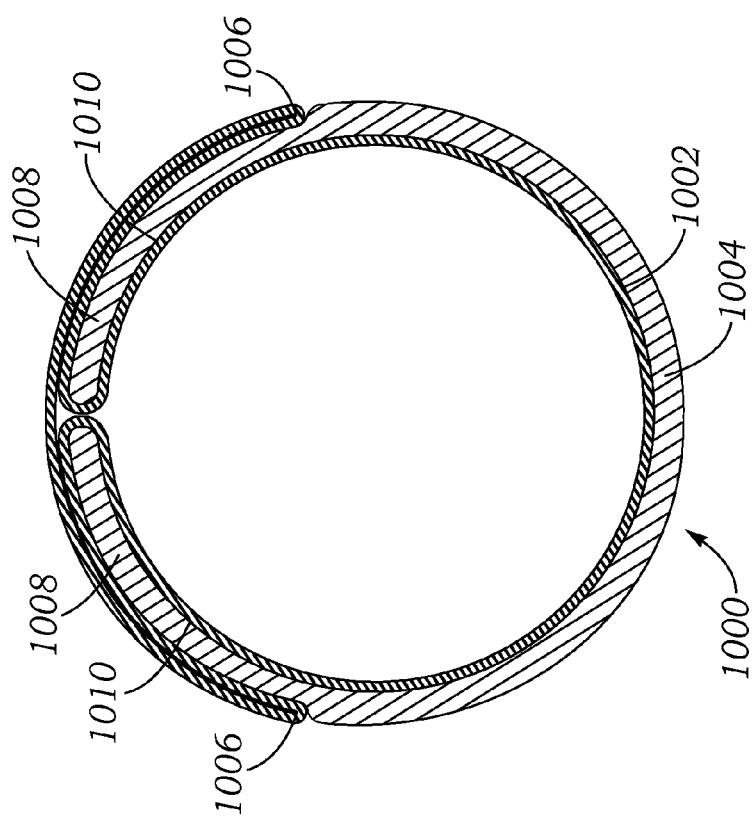

EXPANDABLE SHEATH FOR INTRODUCING AN ENDOVASCULAR DELIVERY DEVICE INTO A BODY

CROSS REFERENCE TO RELATED APPLICATION

The present application is a continuation-in-part of U.S. patent application Ser. No. 12/249,867, filed Oct. 10, 2008, which is hereby incorporated by reference herein in its entirety.

FIELD

The present application concerns embodiments of a sheath for use with catheter-based technologies for repairing and/or replacing heart valves, as well as for delivering a prosthetic device, such as a prosthetic valve to a heart via the patient's vasculature.

BACKGROUND

Endovascular delivery catheter assemblies are used to implant prosthetic devices, such as a prosthetic valve, at locations inside the body that are not readily accessible by surgery or where access without invasive surgery is desirable. For example, aortic, mitral, tricuspid, and/or pulmonary prosthetic valves can be delivered to a treatment site using minimally invasive surgical techniques.

An introducer sheath can be used to safely introduce a delivery apparatus into a patient's vasculature (e.g., the femoral artery). An introducer sheath generally has an elongated sleeve that is inserted into the vasculature and a housing that contains one or more sealing valves that allow a delivery apparatus to be placed in fluid communication with the vasculature with minimal blood loss. A conventional introducer sheath typically requires a tubular loader to be inserted through the seals in the housing to provide an unobstructed path through the housing for a valve mounted on a balloon catheter. A conventional loader extends from the proximal end of the introducer sheath, and therefore decreases the available working length of the delivery apparatus that can be inserted through the sheath and into the body.

Conventional methods of accessing a vessel, such as a femoral artery, prior to introducing the delivery system include dilating the vessel using multiple dilators or sheaths that progressively increase in diameter. This repeated insertion and vessel dilation can increase the amount of time the procedure takes, as well as the risk of damage to the vessel.

Radially expanding intravascular sheaths have been disclosed. Such sheaths tend to have complex mechanisms, such as ratcheting mechanisms that maintain the shaft or sheath in an expanded configuration once a device with a larger diameter than the sheath's original diameter is introduced.

However, delivery and/or removal of prosthetic devices and other material to or from a patient still poses a significant risk to the patient. Furthermore, accessing the vessel remains a challenge due to the relatively large profile of the delivery system that can cause longitudinal and radial tearing of the vessel during insertion. The delivery system can additionally dislodge calcified plaque within the vessels, posing an additional risk of clots caused by the dislodged plaque.

Accordingly, there remains a need in the art for an improved introducer sheath for endovascular systems used for implanting valves and other prosthetic devices.

SUMMARY

Embodiments of the present expandable sheath can minimize trauma to the vessel by allowing for temporary expansion of a portion of the introducer sheath to accommodate a delivery system, followed by a return to the original diameter once the delivery system passes through. Some embodiments can comprise a sheath with a smaller profile than that of prior art introducer sheaths. Furthermore, certain embodiments can reduce the length of time a procedure takes, as well as reduce the risk of a longitudinal or radial vessel tear, or plaque dislodgement because only one sheath is required, rather than several different sizes of sheaths. Embodiments of the present expandable sheath can require only a single vessel insertion, as opposed to requiring multiple insertions for the dilation of the vessel.

One embodiment of a sheath for introducing a prosthetic device comprises an inner layer and an outer layer. At least a portion of the sheath can be designed or configured to locally expand from a first diameter to a second diameter as the prosthetic device is pushed through a lumen of the sheath, and then at least partially return to the first diameter once the prosthetic device has passed through. Some embodiments can additionally include an elastic outer cover disposed about the outer layer.

The inner layer can comprise polytetrafluoroethylene (PTFE), polyimide, polyetheretherketone (PEEK), polyurethane, nylon, polyethylene, polyamide, or combinations thereof. The outer layer can comprise PTFE, polyimide, PEEK, polyurethane, nylon, polyethylene, polyamide, polyether block amides, polyether block ester copolymer, thermoset silicone, latex, poly-isoprene rubbers, high density polyethylene (HDPE), Tecoflex, or combinations thereof. In one exemplary embodiment, the inner layer can comprise PTFE and the outer layer can comprise a combination of HDPE and Tecoflex. If present, the elastic outer cover can include any suitable materials, such as any suitable heat shrink materials. Examples include Pebax, polyurethane, silicone, and/or poly-isoprene.

Disclosed embodiments of a sheath comprise a proximal end and a distal end opposite one another. Some embodiments can include a hemostasis valve at or near the proximal end of the sheath. In some embodiments, the outer diameter of the sheath decreases along a gradient from the proximal end to the distal end of the sheath. In other embodiments, the outer diameter of the sheath is substantially constant along at least a majority of the length of the sheath.

One embodiment of a sheath for introducing a prosthetic device into a body can comprise a continuous inner layer defining a lumen therethrough, the inner layer having a folded portion and a discontinuous outer layer having an overlapping portion and an underlying portion. In some embodiments, the inner layer can have at least two folded portions. The outer layer can be configured so that the overlapping portion overlaps the underlying portion, wherein at least a portion of the folded portion of the inner tubular layer is positioned between the overlapping and underlying portions. At least a portion of the sheath is configured to expand to accommodate the prosthetic device.

In some embodiments, at least a portion of the sheath is configured such that a plurality of segments of the sheath each locally expands one at a time from a rest configuration having a first diameter to an expanded configuration having a second diameter that is larger than the first diameter to facilitate passage of the prosthetic device through the lumen of the inner layer. Each segment can have a length defined along the longitudinal axis of the sheath, and each segment of the sheath can be configured to at least partially return to the first diameter once the prosthetic device has passed through. In some embodiments, when each segment of the sheath is in the expanded configuration, a length of the folded portion corresponding to the length of the segment at least partially unfolds (e.g., by separating and/or straightening). A length of the overlapping portion corresponding to the length of the segment can be configured to move with respect to the underlying portion when each segment of the sheath expands from the rest configuration to the expanded configuration.

In one specific embodiment, the inner layer comprises PTFE and the outer layer comprises HDPE and/or Tecoflex. The inner and outer layers can be thermally fused together in some embodiments. In some embodiments, the inner layer comprises a woven fabric and/or braided filaments such as yarn filaments of PTFE, PET, PEEK, and/or nylon.

Some disclosed expandable sheaths can further include an elastic outer cover disposed on an external surface of the outer layer. The elastic outer cover can comprise, for example, heat shrink tubing. Some sheaths include one or more radiopaque marker or fillers, such as a C-shaped band positioned between the inner and outer layers near the distal end of the sheath. Some embodiments include a soft tip secured to the distal end of the sheath.

In some embodiments, the inner layer can include at least one folded portion and at least one weakened portion. A discontinuous outer layer can have an outer surface and an inner surface and a longitudinal gap, and a portion of the inner layer can extend through the longitudinal gap. The at least one folded portion of the inner layer can be positioned adjacent a portion of the outer surface of the outer layer. In some embodiments, the weakened portion can comprise a score line along at least a portion of the inner layer and/or a slit along at least a portion of the inner layer. The weakened portion can be positioned at the at least one folded portion of the inner layer. In some embodiments, the longitudinal gap can be positioned between a first end and a second end of the outer layer.

In some embodiments, an expandable sheath can include a hydrophilic inner liner defining a generally horseshoe-shaped lumen therethrough, the inner liner including at least two weakened portions and an elastic cover positioned radially outward of the inner liner. In some embodiments, when the sheath is in the expanded configuration, the inner liner splits apart at the weakened portions so as to form a discontinuous inner liner.

Methods of making a sheath are also disclosed. One method includes providing a mandrel having a first diameter, providing a first tube having a second diameter, the second diameter being larger than the first diameter, mounting the first tube on the mandrel, gathering excess material of the first tube and folding the excess material to one side to form a folded portion of the inner layer. A second tube can then be provided, and the second tube can be cut to form a coiled layer. An adhesive can be applied to at least a portion of the coiled layer and the coiled layer can be mounted on the first tube such that the adhesive is positioned between the first tube and the coiled layer. The folded portion can be lifted in order to position a portion of the coiled layer under the folded portion.

Some methods include applying heat to the first tube, coiled layer, and mandrel so as to thermally fuse the first tube and the coiled layer together. In some methods, an elastic outer cover can be secured to the outer surface of the coiled layer. In some methods, a soft tip portion can be coupled to a distal end of the expandable sheath to facilitate passing the expandable sheath through a patient's vasculature.

The foregoing and other features and advantages of the invention will become more apparent from the following detailed description, which proceeds with reference to the accompanying figures.

BRIEF DESCRIPTION OF THE DRAWINGS

FIG. 1 is an elevation view of a sheath according to the present disclosure along with an endovascular delivery apparatus for implanting a prosthetic valve.

FIGS. 32A-32H illustrates section or elevation views of various method steps of the methods shown in FIGS. 30-31.

FIG. 35 is an elevation view of an expandable sheath according to the present disclosure and a representative housing.

FIG. 36 is an enlarged cutaway view of the distal end of the sheath of FIG. 35.

FIG. 41 shows an elevation view of an expandable sheath having an elastic outer cover, according to another embodiment.

FIG. 42 illustrates a section view of the sheath of FIG. 41, taken along line 42-42 in FIG. 41.

FIG. 43 illustrates the section view of the sheath shown in FIG. 42, in an expanded configuration.

FIG. 44 illustrates a section view of another embodiment of an expandable sheath.

FIG. 45 shows an expanded configuration of the sheath of FIG. 44.

FIG. 48 illustrates a section view of another embodiment of an expandable sheath according to the present disclosure.

FIG. 49 illustrates a section view of another embodiment of an expandable sheath.

DETAILED DESCRIPTION

Figure 2A:
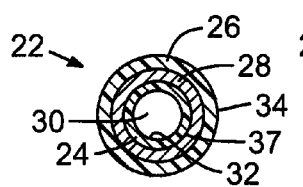
FIGS. 2A, B, and D are section views of embodiments of a sheath for introducing a prosthetic device into a patient.

As used in this application and in the claims, the singular forms "a," "an," and "the" include the plural forms unless the context clearly dictates otherwise. Additionally, the term "includes" means "comprises." Further, the terms "coupled" and "associated" generally means electrically, electromagnetically, and/or physically (e.g., mechanically or chemically) coupled or linked and does not exclude the presence of intermediate elements between the coupled or associated items.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

Moreover, for the sake of simplicity, the attached figures may not show the various ways (readily discernable, based on this disclosure, by one of ordinary skill in the art) in which the disclosed system, method, and apparatus can be used in combination with other systems, methods, and apparatuses. Additionally, the description sometimes uses terms such as "produce" and "provide" to describe the disclosed method. These terms are high-level abstractions of the actual operations that can be performed. The actual operations that correspond to these terms can vary depending on the particular implementation and are, based on this disclosure, readily discernible by one of ordinary skill in the art.

Disclosed embodiments of an expandable sheath can minimize trauma to the vessel by allowing for temporary expansion of a portion of the introducer sheath to accommodate the delivery system, followed by a return to the original diameter once the device passes through. Some embodiments can comprise a sheath with a smaller profile (e.g., a smaller diameter in the rest configuration) than that of prior art introducer sheaths. Furthermore, present embodiments can reduce the length of time a procedure takes, as well as reduce the risk of a longitudinal or radial vessel tear, or plaque dislodgement because only one sheath is required, rather than several different sizes of sheaths. Embodiments of the present expandable sheath can avoid the need for multiple insertions for the dilation of the vessel. Such expandable sheaths can be useful for many types of minimally invasive surgery, such as any surgery requiring introduction of an apparatus into a subject's vessel. For example, the sheath can be used to introduce other types of delivery apparatus for placing various types of intraluminal devices (e.g., stents, prosthetic heart valves, stented grafts, etc.) into many types of vascular and non-vascular body lumens (e.g., veins, arteries, esophagus, ducts of the biliary tree, intestine, urethra, fallopian tube, other endocrine or exocrine ducts, etc.).

FIG. 1 illustrates a sheath 8 according to the present disclosure, in use with a representative delivery apparatus 10, for delivering a prosthetic device 12, such as a tissue heart valve to a patient. The apparatus 10 can include a steerable guide catheter 14 (also referred to as a flex catheter), a balloon catheter 16 extending through the guide catheter 14, and a nose catheter 18 extending through the balloon catheter 16. The guide catheter 14, the balloon catheter 16, and the nose catheter 18 in the illustrated embodiment are adapted to slide longitudinally relative to each other to facilitate delivery and positioning of the valve 12 at an implantation site in a patient's body, as described in detail below. Generally, sheath 8 is inserted into a vessel, such as the transfemoral vessel, passing through the skin of patient, such that the distal end of the sheath 8 is inserted into the vessel. Sheath 8 can include a hemostasis valve at the opposite, proximal end of the sheath.

The delivery apparatus 10 can be inserted into the sheath 8, and the prosthetic device 12 can then be delivered and implanted within patient.

Figure 2B:
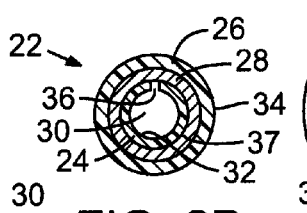
FIG. 2C is a perspective view of one component of such a sheath.
Figure 2C:
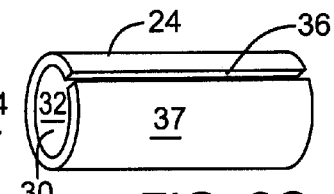
Figure 2D:
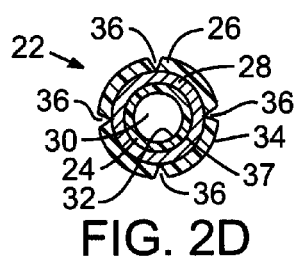

FIGS. 2A, 2B, and 2D show section views of embodiments of a sheath 22 for use with a delivery apparatus such as that shown in FIG. 1. FIG. 2C shows a perspective view of one embodiment of an inner layer 24 for use with the sheath 22. Sheath 22 includes an inner layer, such as inner polymeric tubular layer 24, an outer layer, such as outer polymeric tubular layer 26, and an intermediate tubular layer 28 disposed between the inner and outer polymeric tubular layers 24, 26. The sheath 22 defines a lumen 30 through which a delivery apparatus can travel into a patient's vessel in order to deliver, remove, repair, and/or replace a prosthetic device. Such introducer sheaths 22 can also be useful for other types of minimally invasive surgery, such as any surgery requiring introduction of an apparatus into a subject's vessel. For example, the sheath 22 also can be used to introduce other types of delivery apparatus for placing various types of intraluminal devices (e.g., stents, stented grafts, etc.) into many types of vascular and non-vascular body lumens (e.g., veins, arteries, esophagus, ducts of the biliary tree, intestine, urethra, fallopian tube, other endocrine or exocrine ducts, etc.).

The outer polymeric tubular layer 26 and the inner polymeric tubular layer 24 can comprise, for example, PTFE (e.g. Teflon®), polyimide, PEEK, polyurethane, nylon, polyethylene, polyamide, polyether block amides (e.g. PEBAX®), polyether block ester copolymer, polyesters, fluoropolymers, polyvinyl chloride, thermoset silicone, latex, poly-isoprene rubbers, polyolefin, other medical grade polymers, or combinations thereof. The intermediate tubular layer 28 can comprise a shape memory alloy such as Nitinol, and/or stainless steel, cobalt chromium, spectra fiber, polyethylene fiber, aramid fiber, or combinations thereof.

The inner polymeric tubular layer 24 can advantageously be provided with a low coefficient of friction on its inner surface. For example, the inner polymeric tubular layer 24 can have a coefficient of friction of less than about 0.1. Some embodiments of a sheath 22 can include a lubricious liner on the inner surface 32 of the inner polymeric tubular layer 24. Such a liner can facilitate passage of a delivery apparatus through the lumen 30 of the sheath 22. Examples of suitable lubricious liners include materials that can reduce the coefficient of friction of the inner polymeric tubular layer 24, such as PTFE, polyethylene, polyvinylidine fluoride, and combinations thereof. Suitable materials for a lubricious liner also include other materials desirably having a coefficient of friction of about 0.1 or less.

The inner diameter of the intermediate tubular layer 28 varies depending on the application and size of the delivery apparatus and prosthetic device. In some embodiments, the inner diameter ranges from about 0.005 inches to about 0.400 inches. The thickness of the intermediate tubular layer 28 can be varied depending on the desired amount of radial expansion, as well as the strength required. For example, the thickness of the intermediate tubular layer 28 can be from about 0.002 inches to about 0.025 inches. The thicknesses of the inner polymeric tubular layer 24 and the outer polymeric tubular layer 26 can also be varied depending on the particular application of the sheath 22. In some embodiments, the thickness of the inner polymeric tubular layer 24 ranges from about 0.0005 inches to about 0.010 inches, and in one particular embodiment, the thickness is about 0.002 inches. Outer polymeric tubular layers 26 can have a thickness of from about 0.002 inches to about 0.015 inches, and in one particular embodiment the outer polymeric tubular layer 26 has a thickness of about 0.010 inches.

The hardness of each layer of the sheath 22 can also be varied depending on the particular application and desired properties of the sheath 22. In some embodiments, the outer polymeric tubular layer 26 has a Shore hardness of from about 25 Durometer to about 75 Durometer.

Additionally, some embodiments of a sheath 22 can include an exterior hydrophilic coating on the outer surface 34 of the outer polymeric tubular layer 26. Such a hydrophilic coating can facilitate insertion of the sheath 22 into a patient's vessel. Examples of suitable hydrophilic coatings include the Harmony™ Advanced Lubricity Coatings and other Advanced Hydrophilic Coatings available from SurModics, Inc., Eden Prairie, Minn. DSM medical coatings (available from Koninklijke DSM N. V, Heerlen, the Netherlands), as well as other hydrophilic coatings, are also suitable for use with the sheath 22.

In some embodiments, the outer surface 34 of the outer polymeric tubular layer 26 can be modified. For example, surface modifications such as plasma etching can be performed on the outer surface 34. Similarly, other surfaces, both outer and inner, can be surface modified according to certain embodiments and desired application. In some embodiments, surface modification can improve adhesion between the layers in the areas of the modification.

The sheath 22 also can have at least one radiopaque filler or marker. The radiopaque filler or marker can be associated with the outer surface 34 of the outer polymeric tubular layer 26. Alternatively, the radiopaque filler or marker can be embedded or blended within the outer polymeric tubular layer 24. Similarly, the radiopaque filler or marker can be associated with a surface of the inner polymeric tubular layer 24 or the intermediate tubular layer 28 or embedded within either or both of those layers.

Suitable materials for use as a radiopaque filler or marker include, for example, barium sulfite, bismuth trioxide, titanium dioxide, bismuth subcarbonate, or combinations thereof. The radiopaque filler can be mixed with or embedded in the material used to form the outer polymeric tubular layer 26, and can comprise from about 5% to about 45% by weight of the outer polymeric tubular layer. More or less radiopaque material can be used in some embodiments, depending on the particular application.

In some embodiments, the inner polymeric tubular layer 24 can comprise a substantially uniform cylindrical tube. In alternative embodiments, the inner polymeric tubular layer 24 can have at least one section of discontinuity along its longitudinal axis to facilitate radial expansion of the inner polymeric tubular layer 24. For example, the inner polymeric tubular layer 24 can be provided with one or more longitudinal notches and/or cuts 36 extending along at least a portion of the length of the sheath 22. Such notches or cuts 36 can facilitate radial expansion of the inner polymeric tubular layer 24, thus accommodating passage of a delivery apparatus or other device. Such notches and/or cuts 36 can be provided near the inner surface 32, near the outer surface 37, and/or substantially through the entire thickness of the inner polymeric layer 24. In embodiments with a plurality of notches and/or cuts 36, such notches and/or cuts 36 can be positioned such that they are substantially equally spaced from one another circumferentially around the inner polymeric layer 24. Alternatively, notches and cuts 36 can be spaced randomly in relation to one another, or in any other desired pattern. Some or all of any provided notches and/or cuts 36 can extend longitudinally along substantially the entire length of the sheath 22. Alternatively, some or all of any provided notches and/or cuts 36 can extend longitudinally only along a portion of the length of the sheath 22.

As shown in FIGS. 2B and 2C (which illustrates only the inner polymeric tubular layer 24), in some embodiments, the inner polymeric tubular layer 24 contains at least one notch or cut 36 that extends longitudinally and parallel to an axis defined by the lumen 30, extending substantially the entire length of the sheath 22. Thus, upon introduction of a delivery apparatus, the inner polymeric tubular layer 24 can split open along the notch and/or cut 36 and expand, thus accommodating the delivery apparatus.

Additionally or alternatively, as shown in FIG. 2D, the outer polymeric tubular layer 26 can comprise one or more notches and/or cuts 36. Notches and/or cuts 36, in some embodiments, do not extend through the entire thickness of the outer tubular layer 26. The notches and/or cuts 36 can be separable upon radial expansion of the sheath 22. The outer polymeric tubular layer 26 can be retractable longitudinally, or able to be pulled back away from the intermediate tubular layer 28 and the inner polymeric tubular layer 24. In embodiments with a retractable outer polymeric tubular layer 26, the outer polymeric tubular layer 26 can be retracted to accommodate or facilitate passage of a delivery apparatus through the lumen 30, and then can be replaced to its original position on the sheath 22.

Figure 3:
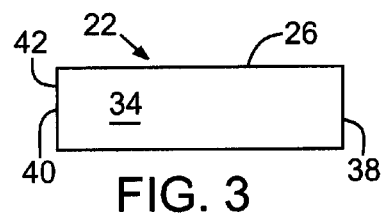
FIG. 3 is an elevation view of the sheath shown in FIG. 2.

FIG. 3 illustrates an elevation view of the sheath 22 shown in FIG. 2A. In this view, only the outer polymeric tubular layer 26 is visible. The sheath 22 comprises a proximal end 38 and a distal end 40 opposite the proximal end 38. The sheath 22 can include a hemostasis valve inside the lumen of the sheath 22, at or near the proximal end 38 of the sheath 22. Additionally, the sheath 22 can comprise a soft tip 42 at the distal end 40 of the sheath 22. Such a soft tip 42 can be provided with a lower hardness than the other portions of the sheath 22. In some embodiments, the soft tip 42 can have a Shore hardness from about 25 D to about 40 D.

Figure 4A:
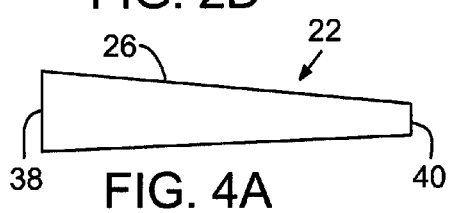
FIGS. 4A-4B are elevation views of two embodiments of a sheath according to the present disclosure, having varying outer diameters.
Figure 4B:
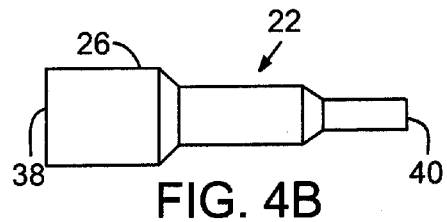

As shown in FIG. 3, the unexpanded original outer diameter of the sheath 22 can be substantially constant across the length of the sheath 22, substantially from the proximal end 38 to the distal end 40. In alternative embodiments, such as the ones illustrated in FIGS. 4A-4B, the original unexpanded outer diameter of the sheath 22 can decrease from the proximal end 38 to the distal end 40. As shown in the embodiment in FIG. 4A, the original unexpanded outer diameter can decrease along a gradient, from the proximal end 38 to the distal end 40. In alternative embodiments, such as the one shown in FIG. 4B, the original unexpanded outer diameter of sheath 22 can incrementally step down along the length of the sheath 22, wherein the largest original unexpanded outer diameter is near the proximal end 38 and the smallest original unexpanded outer diameter is near the distal end 40 of the sheath 22.

Figure 5:
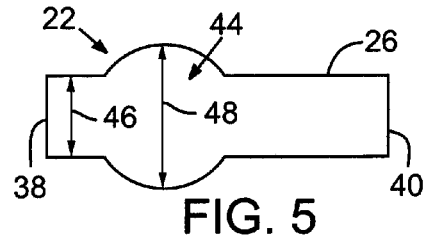
FIG. 5 illustrates an elevation view of one embodiment of a sheath, expanded at a first location to accommodate a delivery system.
Figure 6:
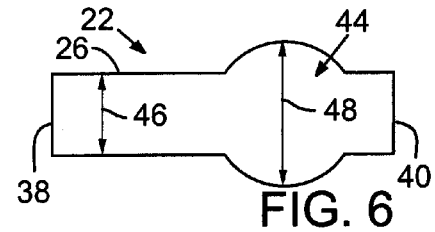
FIG. 6 shows an elevation view of the sheath of claim 5, expanded at a second location, farther down the sheath.

As shown in FIGS. 5-6, the sheath 22 can be designed to locally expand as the prosthetic device is passed through the lumen of the sheath 22, and then substantially return to its original shape once the prosthetic device has passed through that portion of the sheath 22. For example, FIG. 5 illustrates a sheath 22 have a localized bulge 44, representative of a device being passed through the internal lumen of the sheath 22. FIG. 5 shows the device close to the proximal end 38 of the sheath 22, close to the area where the device is introduced into the sheath 22. FIG. 6 shows the sheath 22 of FIG. 5, with the device having progressed further along the sheath 22. The localized bulge 44 is now closer to the distal end 40 of the sheath 22, and thus is about to be introduced to a patient's vessel. As evident from FIGS. 5 and 6, once the localized bulge associated with the device has passed through a portion of the lumen of the sheath 22, that portion of the sheath 22 can automatically return to its original shape and size, at least in part due to the materials and structure of the sheath 22.

The sheath 22 has an unexpanded inner diameter equal to the inner diameter of the inner polymeric tubular layer (not visible in FIGS. 5-6), and an unexpanded outer diameter 46 equal to the outer diameter of the outer polymeric tubular layer 26. The sheath 22 is designed to be expanded to an expanded inner diameter and an expanded outer diameter 48 which are larger than the unexpanded inner diameter and the unexpanded outer diameter 46, respectively. In one representative embodiment, the unexpanded inner diameter is about 16 Fr and the unexpanded outer diameter 46 is about 19 Fr, while the expanded inner diameter is about 26 Fr and the expanded outer diameter 48 is about 29 Fr. Different sheaths 22 can be provided with different expanded and unexpanded inner and outer diameters, depending on the size requirements of the delivery apparatus for various applications. Additionally, some embodiments can provide more or less expansion depending on the particular design parameters, the materials, and/or configurations used.

Figure 7:
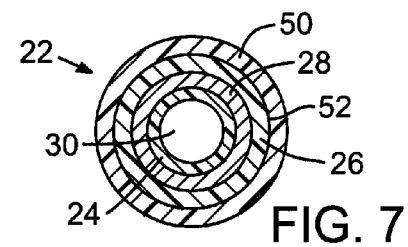
FIG. 7 shows a section view of another embodiment of a sheath that further comprises an outer covering or shell.
Figure 8:
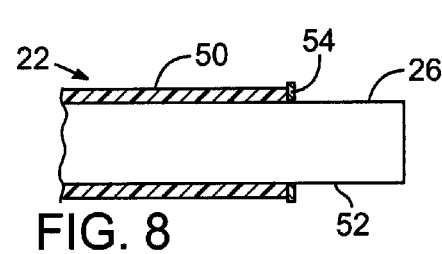
FIG. 8 illustrates an elevation view of one embodiment of a sheath with an outer covering or shell.
Figure 9:
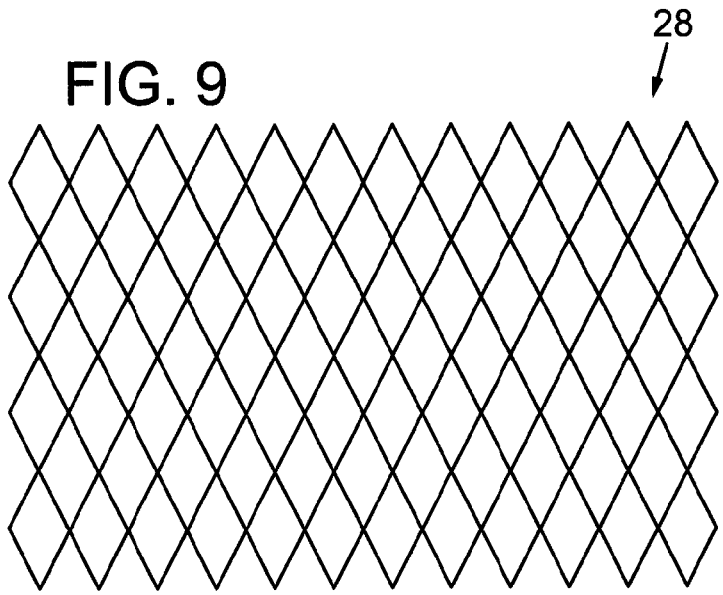
FIG. 9 illustrates a partial elevation view of one embodiment of an intermediate tubular layer that can be used to construct a sheath according to the present disclosure.
Figure 10:
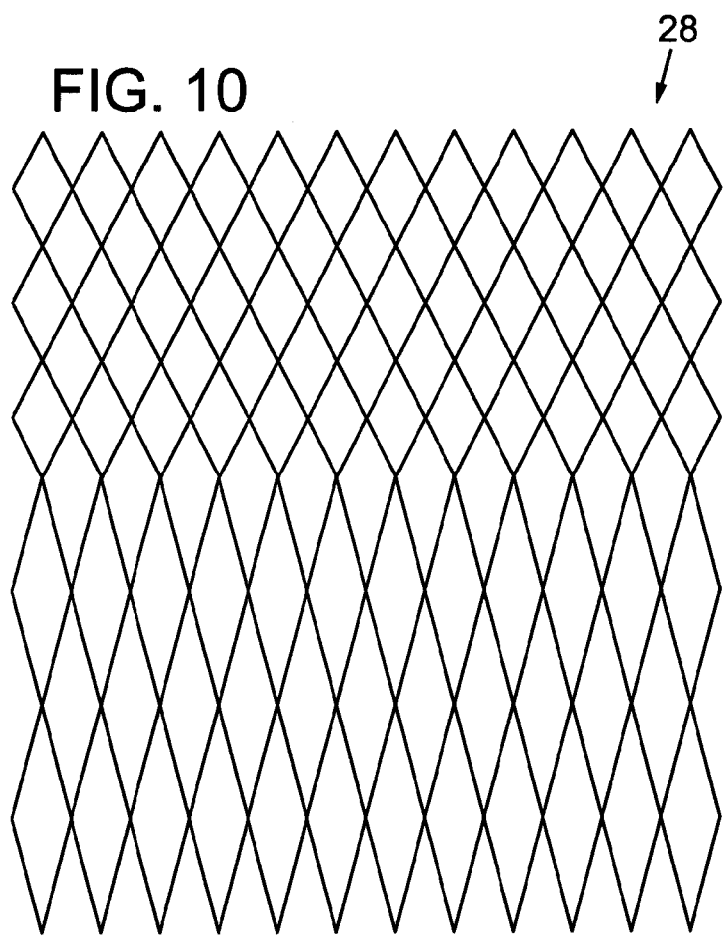
FIG. 10 illustrates a partial elevation view of another embodiment of an intermediate tubular layer having a variable diamond design.
Figure 11:
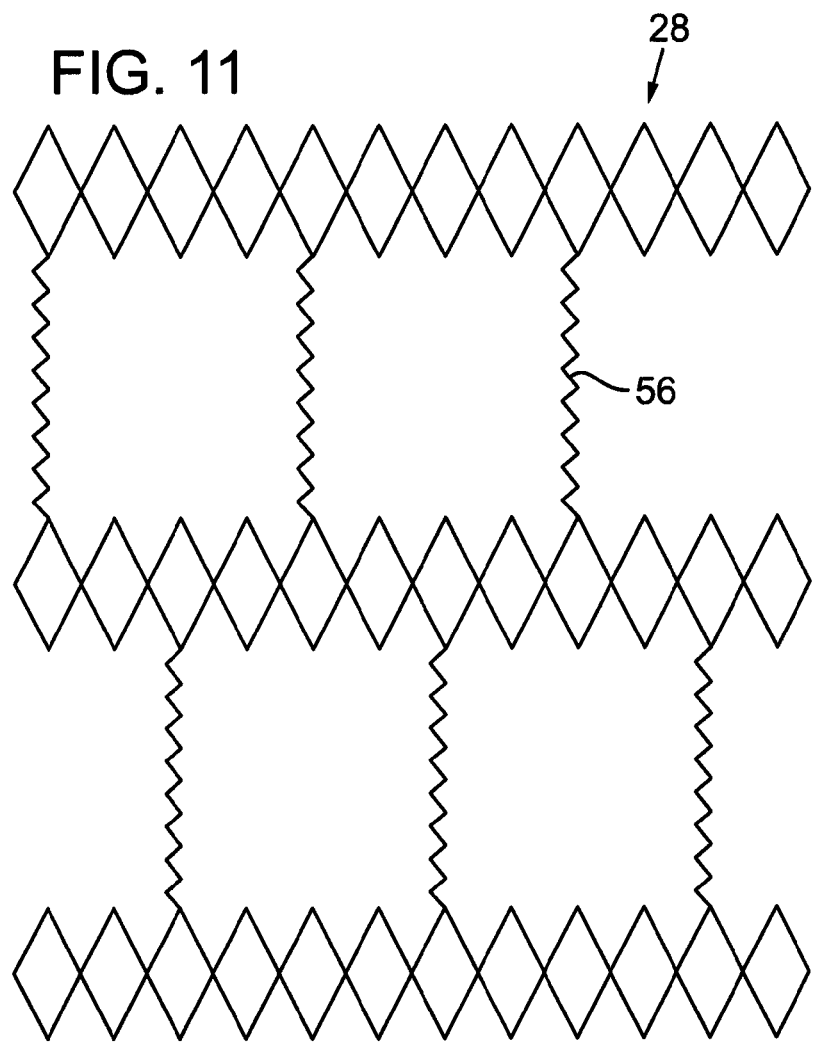
FIG. 11 illustrates a partial elevation view of another embodiment of an intermediate tubular layer having a diamond design with spring struts.
Figure 12:
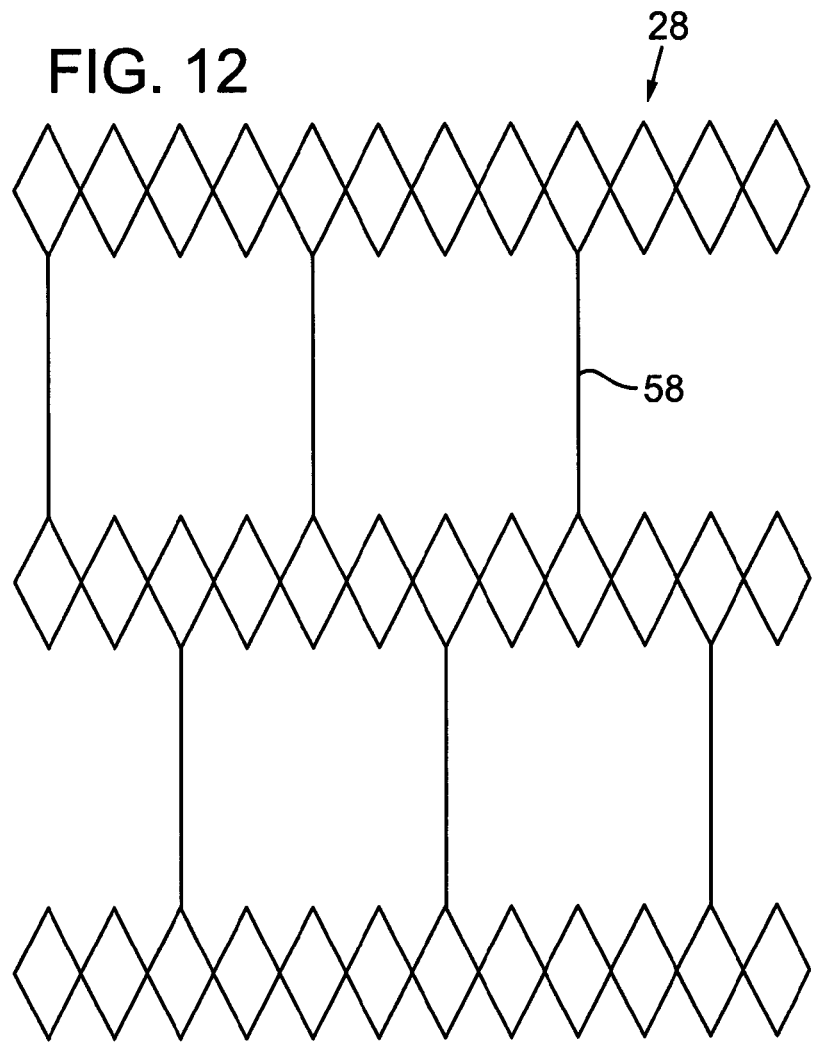
FIG. 12 illustrates a partial elevation view of another embodiment of an intermediate tubular layer having a diamond design with straight struts.
Figure 13:
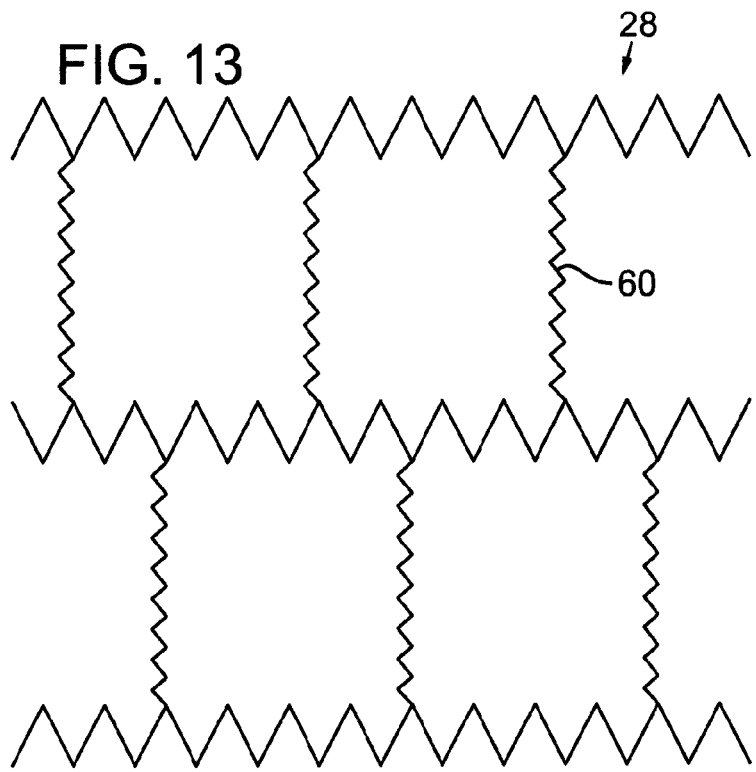
FIG. 13 illustrates a partial elevation view of another embodiment of an intermediate tubular layer having a saw tooth design with spring struts.
Figure 14:
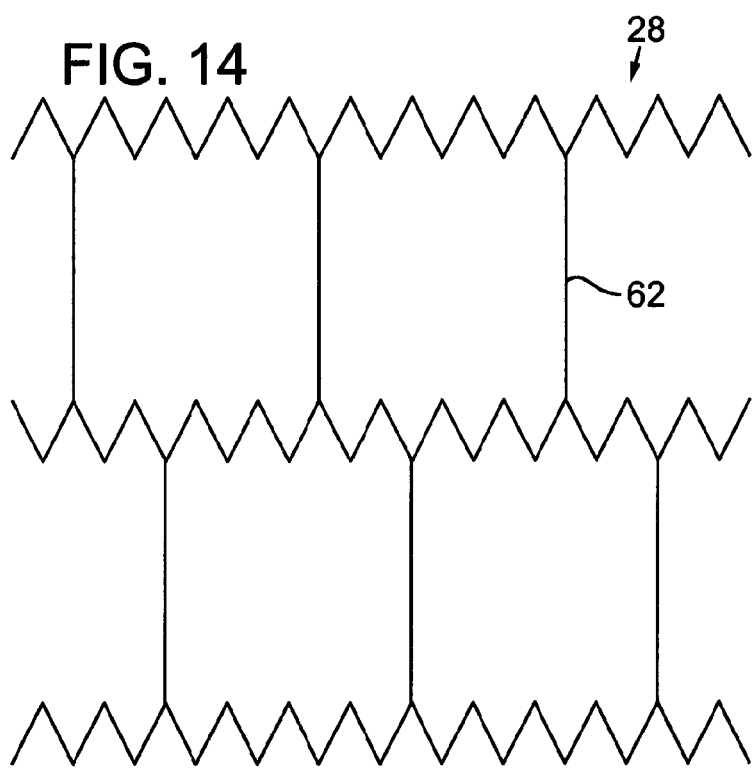
FIG. 14 illustrates a partial elevation view of another embodiment of an intermediate tubular layer having a saw tooth design with straight struts.
Figure 15:
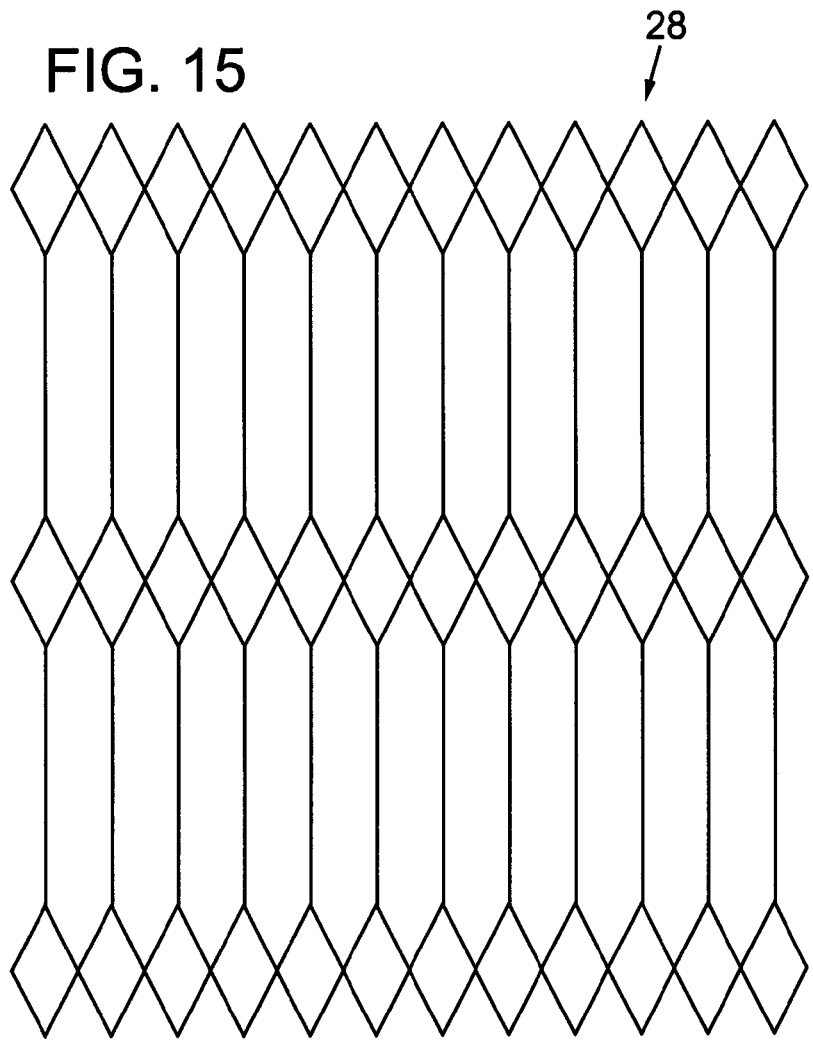
FIG. 15 illustrates a partial elevation view of another embodiment of an intermediate tubular layer having a diamond design with straight struts.
Figure 16:
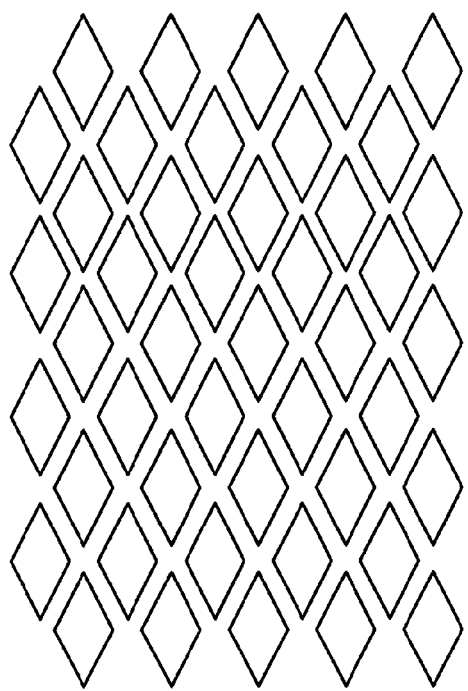
FIG. 16 illustrates a partial elevation view of another embodiment of an intermediate tubular layer having a helical or spiral design.
Figure 17:
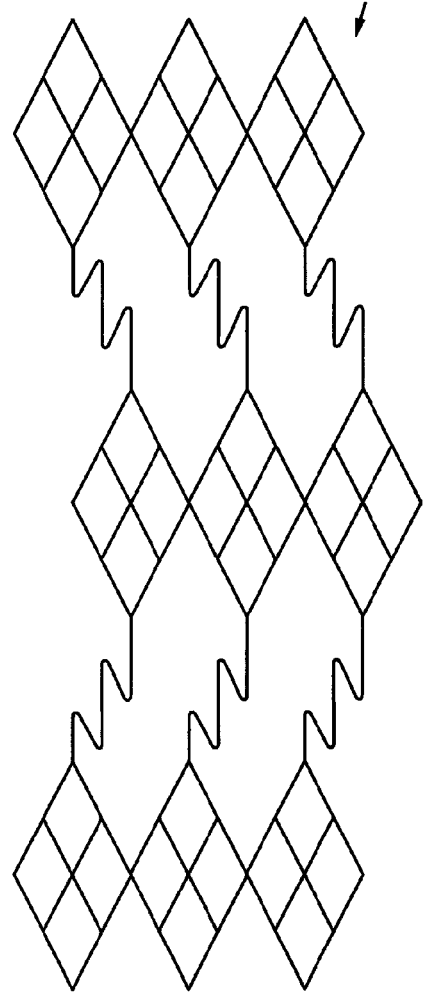
FIG. 17 illustrates a partial elevation view of another embodiment of an intermediate tubular layer having a diamond design with non-straight struts.
Figure 18:
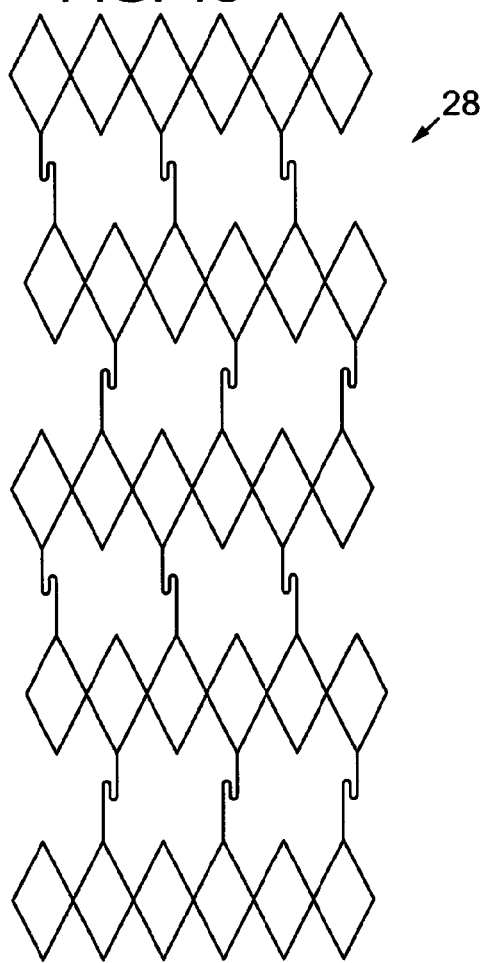
FIG. 18 illustrates a partial elevation view of another embodiment of an intermediate tubular layer having an alternative diamond design with non-straight struts.
Figure 19:
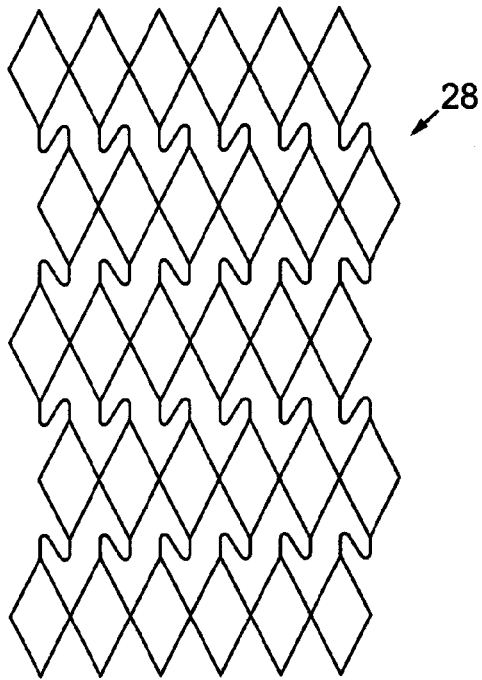
FIG. 19 illustrates a partial elevation view of another embodiment of an intermediate tubular layer having yet another diamond design with non-straight struts.
Figure 20:
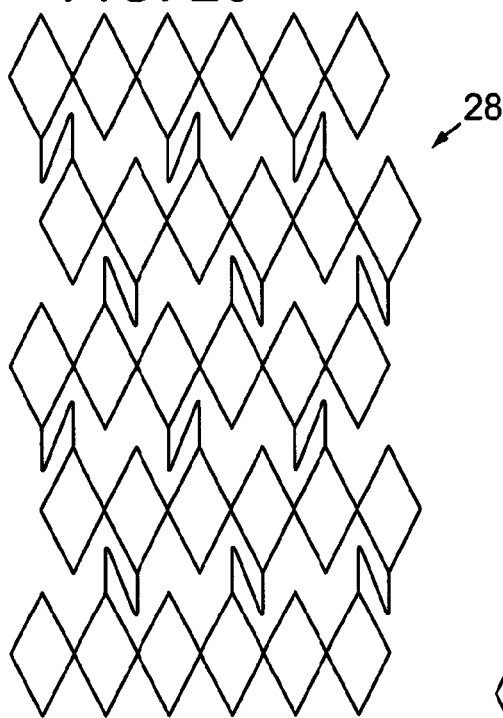
FIG. 20 illustrates a partial elevation view of another embodiment of an intermediate tubular layer having a diamond design with struts.
Figure 21:
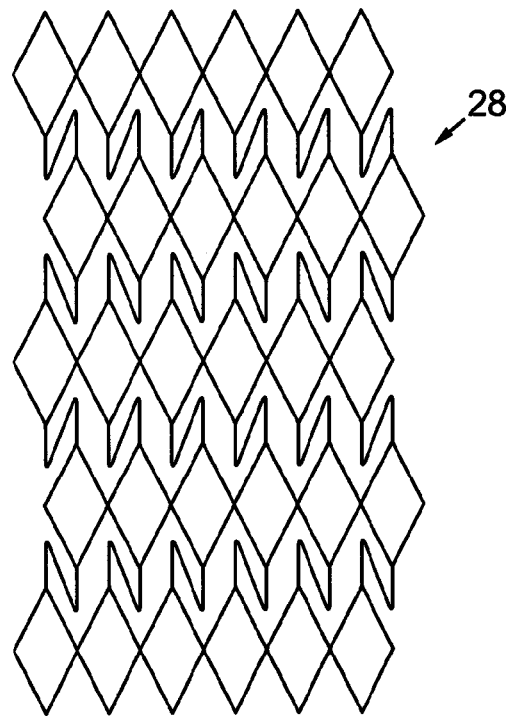
FIG. 21 illustrates a partial elevation view of another embodiment of an intermediate tubular layer having a design similar to that shown in FIG. 20, but with additional struts.
Figure 22:
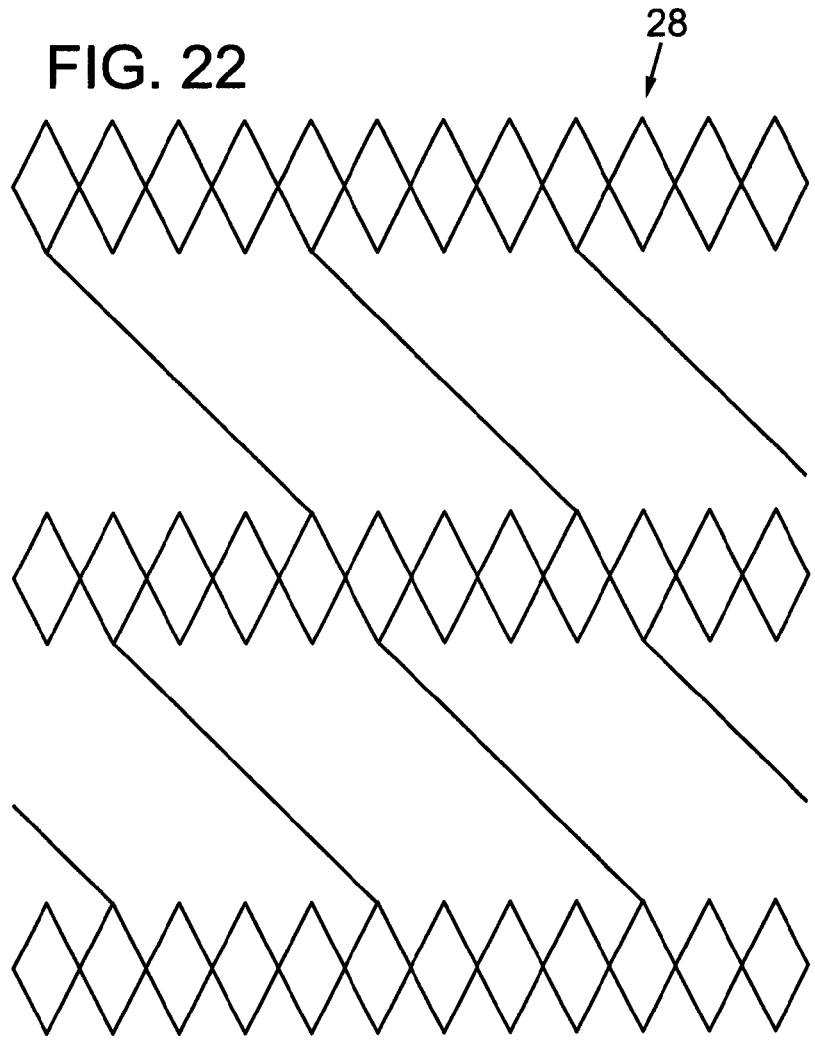
FIG. 22 illustrates a partial elevation view of another embodiment of an intermediate tubular layer having a diamond design with spiral struts.
Figure 23:
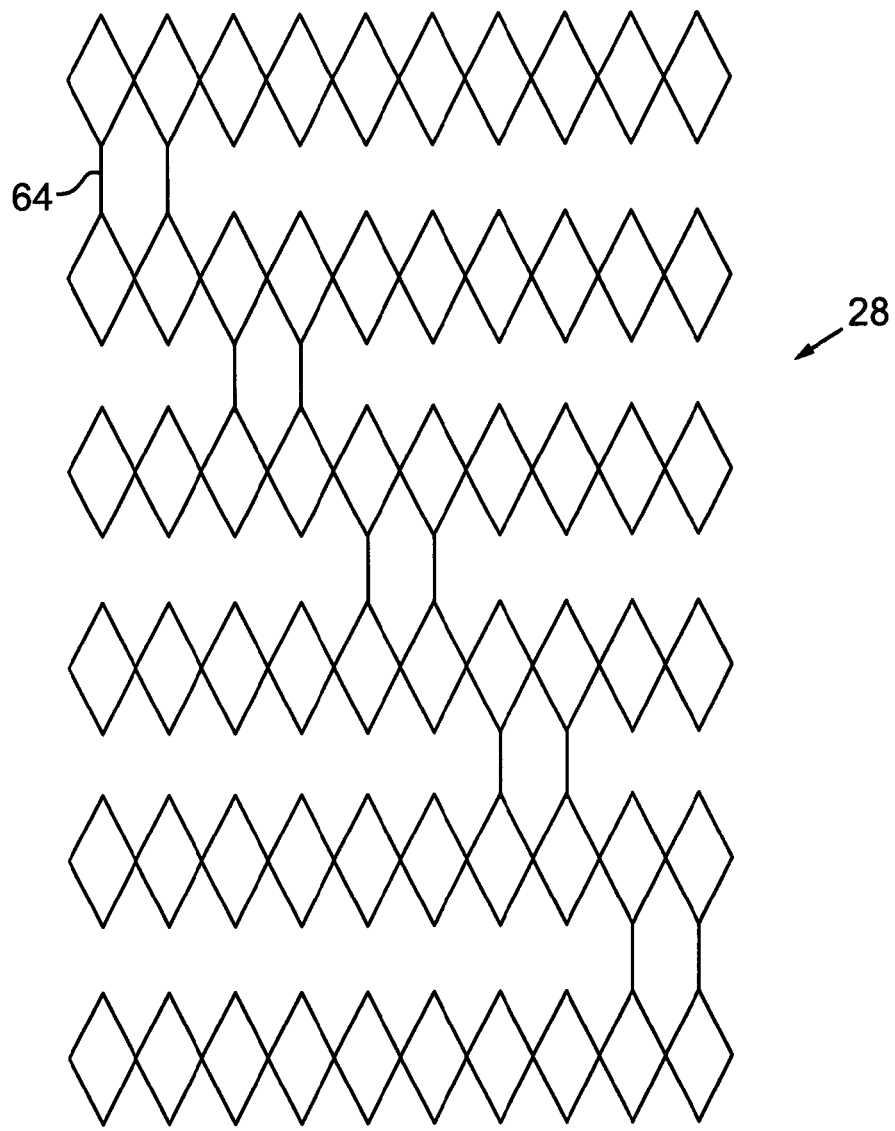
FIG. 23 illustrates a partial elevation view of another embodiment of an intermediate tubular layer having a diamond design with adjacent struts.

In some embodiments of a sheath according to the present disclosure, and as shown in section in FIG. 7 and in elevation in FIG. 8, the sheath 22 can additionally comprise an outer covering, such as outer polymeric covering 50, disposed on the outer surface 52 of the outer polymeric tubular layer 26. The outer polymeric covering 50 can provide a protective covering for the underlying sheath 22. In some embodiments, the outer polymeric covering 50 can contain a self-expandable sheath in a crimped or constrained state, and then release the self-expandable sheath upon removal of the outer polymeric covering 50. For example, in some embodiments of a self-expandable sheath, the intermediate layer 28 can comprise Nitinol and/or other shape memory alloys, and the intermediate layer 28 can be crimped or radially compressed to a reduced diameter within the outer polymeric tubular layer 26 and the outer polymeric covering 50. Once the self-expandable sheath is at least partially inserted into a patient's vessel, the outer polymeric covering 50 can be slid back, peeled away, or otherwise at least partially removed from the sheath. To facilitate removal of the outer polymeric covering 50, a portion of the outer polymeric covering 50 can remain outside the patient's vessel, and that portion can be pulled back or removed from the sheath to allow the sheath to expand. In some embodiments, substantially the entire outer polymeric covering 50 can be inserted, along with the sheath, into a patient's vessel. In these embodiments, an external mechanism attached to the outer polymeric covering 50 can be provided, such that the outer polymeric covering can be at least partially removed from the sheath once the sheath is inserted into a patient's vessel.

Once no longer constrained by the outer polymeric covering 50, the radially compressed intermediate layer 28 can self-expand, causing expansion of the sheath along the length of the intermediate layer 28. In some embodiments, portions of the sheath can radially collapse, at least partially returning to the original crimped state, as the sheath is being withdrawn from the vessel after completion of the surgical procedure. In some embodiments, such collapse can be facilitated and/or encouraged by an additional device or layer that, in some embodiments, can be mounted onto a portion of the sheath prior to the sheath's insertion into the vessel.

The outer polymeric covering 50, in some embodiments, is not adhered to the other layers of the sheath 22. For example, the outer polymeric covering 50 may be slidable with respect to the underlying sheath, such that it can be easily removed or retracted from its initial position on the sheath 22.

As seen in FIG. 8, the outer polymeric covering 50 can include one or more peel tabs 54 to facilitate manual removal of the outer polymeric covering 50. The outer polymeric covering 50 can be automatically or manually retractable and/or splittable to facilitate radial expansion of the sheath 22. Peel tabs 54 can be located approximately 90 degrees from any cut or notch present in the outer polymeric covering 50, and approximately 180 degrees offset from one another. In alternative embodiments, the peel tabs 54 can extend substantially around the circumference of the outer polymeric covering 50, thus resulting in a single circular peel tab 54.

Suitable materials for the outer polymeric covering 50 are similar to those materials suitable for the inner polymeric tubular layer and the outer polymeric tubular layer, and can include PTFE and/or high density polyethylene.

Turning now to the intermediate tubular layer 28, several different configurations are possible. The intermediate tubular layer 28 is generally a thin, hollow, substantially cylindrical tube comprising an arrangement, pattern, structure, or configuration of wires or struts, however other geometries can also be used. The intermediate tubular layer 28 can extend along substantially the entire length of the sheath 22, or alternatively, can extend only along a portion of the length of sheath 22. Suitable wires can be round, ranging from about 0.0005 inches thick to about 0.10 inches thick, or flat, ranging from about 0.0005 inches×0.003 inches to about 0.003 inches×0.007 inches. However, other geometries and sizes are also suitable for certain embodiments. If braided wire is used, the braid density can be varied. Some embodiments have a braid density of from about thirty picks per inch to about eighty picks per inch and can include up to thirty-two wires in various braid patterns.

One representative embodiment of an intermediate tubular layer comprises a braided Nitinol composite which is at least partially encapsulated by an inner polymeric tubular member and an outer polymeric tubular member disposed on inner and outer surfaces of the intermediate tubular layer, respectively. Such encapsulation by polymeric layers can be accomplished by, for example, fusing the polymeric layers to the intermediate tubular layer, or dip coating the intermediate tubular layer. In some embodiments, an inner polymeric tubular member, an intermediate tubular layer, and an outer polymeric tubular layer can be arranged on a mandrel, and the layers can then be thermally fused or melted into one another by placing the assembly in an oven or otherwise heating it. The mandrel can then be removed from the resulting sheath. In other embodiments, dip coating can be used to apply an inner polymeric tubular member to the surface of a mandrel. The intermediate tubular layer can then be applied, and the inner polymeric tubular member allowed to cure. The assembly can then be dip coated again, such as to apply a thin coating of, for example, polyurethane, which will become the outer polymeric tubular member of the sheath. The sheath can then be removed from the mandrel.

Additionally, the intermediate tubular layer 28 can be, for example, braided or laser cut to form a pattern or structure, such that the intermediate tubular layer 28 is amenable to radial expansion. FIGS. 9-23 illustrate partial elevation views of various structures for the intermediate tubular layer. Some illustrated structures, such as those shown in FIGS. 11-14 and 23, include at least one discontinuity. For example, the struts 56, 58, 60, 62, 64 shown in FIGS. 11, 12, 13, 14, and 23, respectively, result in a discontinuous intermediate tubular layer 28 in that the struts 56, 58, 60, 62, 64 separate adjacent sections of the intermediate tubular layer 28 from each other, where the sections are spaced apart from each other along a longitudinal axis parallel to the lumen of the sheath. Thus, the structure of the intermediate tubular layer 28 can vary from section to section, changing along the length of the sheath.

The structures shown in FIGS. 9-23 are not necessarily drawn to scale. Components and elements of the structures can be used alone or in combination within a single intermediate tubular layer 28. The scope of the intermediate tubular layer 28 is not meant to be limited to these particular structures; they are merely exemplary embodiments.

Figure 24:
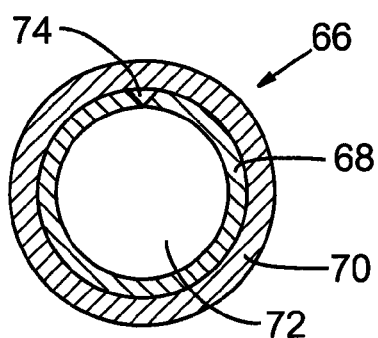
FIG. 24 illustrates a section view of one embodiment of a sheath having a longitudinal notch.
Figure 25:
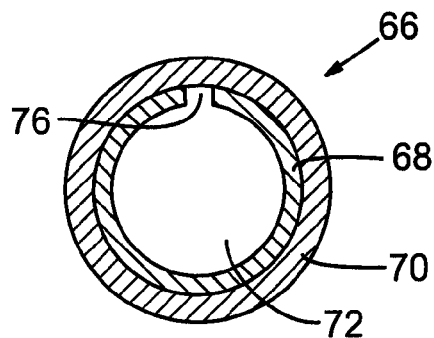
FIG. 25 shows a section view of one embodiment of a sheath having a longitudinal cut in the inner layer.
Figure 26:
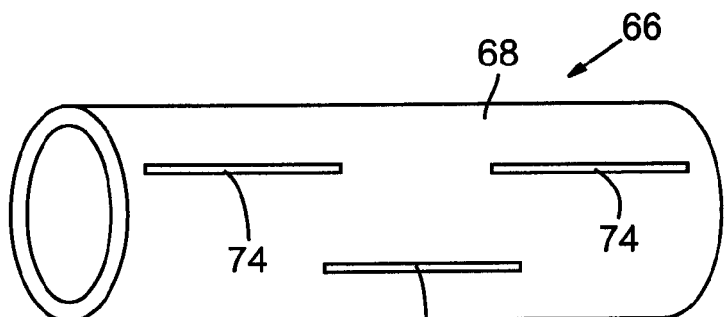
FIG. 26 shows a perspective view of one embodiment of a sheath having a plurality of notches or cuts in the outer tubular layer.

Alternative embodiments of a sheath for introducing a prosthetic device are also described. For example, FIGS. 24-26 illustrate a section view and a perspective view, respectively, of a sheath 66 for introducing a prosthetic device into a body. The sheath 66 comprises an inner layer, such as inner polymeric layer 68, an outer layer, such as polymeric tubular layer 70, and a hemostasis valve (not shown). The inner polymeric layer 68 and the outer polymeric tubular layer 70 at least partially enclose a lumen 72, through which a delivery apparatus and prosthetic device can pass from outside the patient's body into the patient's vessel. Either or both of the inner polymeric layer 68 and the outer polymeric layer 70 can be provided with at least one longitudinal notch and/or cut to facilitate radial expansion of the sheath.

For example, FIG. 24 illustrates a longitudinal notch 74 in the inner polymeric layer 68 that can facilitate radial expansion of the sheath 66. The longitudinal notch 74 can separate or split open completely upon application of a radial force due to insertion of a delivery apparatus or prosthetic device. Similarly, FIG. 25 illustrates a longitudinal cut 76 in the inner polymeric layer 68 that can also facilitate radial expansion of the sheath 66. The outer polymeric layer 70 can, additionally or alternatively, comprise one or more longitudinal cuts 76 or notches 74. Such cuts and/or notches, whether in the inner polymeric layer 68 or the outer polymeric layer 70, can extend substantially through the entire thickness of the layer, or can extend only partially through the thickness of the layer. The cuts and/or notches can be positioned at or near the inner or outer surface, or both surfaces, of the inner and/or outer polymeric layers 68, 70.

FIG. 26 illustrates a perspective view of one embodiment of an inner polymeric layer 68 with longitudinal notches 74 and a longitudinal cut 76. More or fewer notches 74 and/or cuts 76 can be provided. For clarity, the outer polymeric layer 70 is not shown in FIG. 26. As shown in FIG. 26, longitudinal notches 74 and/or cuts 76 can extend only along a portion of the length of sheath 66. In alternative embodiments, one or more notches 74 and/or cuts 76 can extend substantially along the entire length of the sheath 66. Additionally, notches 74 and/or cuts 76 can be positioned randomly or patterned.

One particular embodiment of a sheath 66 comprises a sheath having a notch or cut in the outer polymeric layer 70 or the inner polymeric layer 68 that extends longitudinally along approximately 75% of the length of the sheath 66. If such a notch or cut extends only partially through the associated layer, it can have a relatively low tear force, such as a tear force of about 0.5 lbs., so that the notch splits open relatively easily during use.

The inner polymeric layer 68 and the outer polymeric layer 70 can optionally be adhered together or otherwise physically associated with one another. The amount of adhesion between the inner polymeric layer 68 and the outer polymeric layer 70 can be variable over the surfaces of the layers. For example, little to no adhesion can be present at areas around or near any notches and/or cuts present in the layers, so as not to hinder radial expansion of the sheath 66. Adhesion between the layers can be created by, for example, thermal bonding and/or coatings. Embodiments of a sheath 66 can be formed from an extruded tube, which can serve as the inner polymeric layer 68. The inner polymeric layer 68 can be surface treated, such as by plasma etching, chemical etching or other suitable methods of surface treatment. By treating the surface of the inner polymeric layer 68, the outer surface of the inner polymeric layer 68 can have areas with altered surface angles that can provide better adhesion between the inner polymeric layer 68 and the outer polymeric layer 70. The treated inner polymeric layer can be dip coated in, for example, a polyurethane solution to form the outer polymeric layer 70. In some configurations, the polyurethane may not adhere well to untreated surface areas of the inner polymeric layer 68. Thus, by surface treating only surface areas of the inner polymeric layer 68 that are spaced away from the areas of expansion (e.g. the portion of the inner polymeric layer 68 near notches 74 and/or cuts 76), the outer polymeric layer 70 can be adhered to some areas of the inner polymeric layer 68, while other areas of the inner polymeric layer 68 remain free to slide relative to the outer polymeric layer 70, thus allowing for expansion of the diameter of the sheath 66. Thus, areas around or near any notches 74 and/or cuts 76 can experience little to no adhesion between the layers, while other areas of the inner and outer polymeric layers 68, 70 can be adhesively secured or otherwise physically associated with each other.

As with previously disclosed embodiments, the embodiments illustrated in FIGS. 24-26 can be applied to sheaths having a wide variety of inner and outer diameters. Applications can utilize a sheath of the present disclosure with an inner diameter of the inner polymeric layer 68 that is expandable to an expanded diameter of from about 3 Fr to about 26 Fr. The expanded diameter can vary slightly along the length of the sheath 66. For example, the expanded outer diameter at the proximal end of the sheath 66 can range from about 3 Fr to about 28 Fr, while the expanded outer diameter at the distal end of the sheath 66 can range from about 3 Fr to about 25 Fr. Embodiments of a sheath 66 can expand to an expanded outer diameter that is from about 10% greater than the original unexpanded outer diameter to about 100% greater than the original unexpanded outer diameter.

In some embodiments, the outer diameter of the sheath 66 gradually decreases from the proximal end of the sheath 66 to the distal end of the sheath 66. For example, in one embodiment, the outer diameter can gradually decrease from about 26 Fr at the proximal end to about 18 Fr at the distal end. The diameter of the sheath 66 can transition gradually across substantially the entire length of the sheath 66. In other embodiments, the transition or reduction of the diameter of the sheath 66 can occur only along a portion of the length of the sheath 66. For example, the transition can occur along a length from the proximal end to the distal end, where the length can range from about 0.5 inches to about the entire length of sheath 66.

Suitable materials for the inner polymeric layer 68 can have a high elastic strength and include materials discussed in connection with other embodiments, especially Teflon (PTFE), polyethylene (e.g. high density polyethylene), fluoropolymers, or combinations thereof. In some embodiments, the inner polymeric layer 68 preferably has a low coefficient of friction, such as a coefficient of friction of from about 0.01 to about 0.5. Some preferred embodiments of a sheath 66 comprise an inner polymeric layer 68 having a coefficient of friction of about 0.1 or less.

Likewise, suitable materials for the outer polymeric layer 70 include materials discussed in connection with other embodiments, and other thermoplastic elastomers and/or highly elastic materials.

The Shore hardness of the outer polymeric layer 70 can be varied for different applications and embodiments. Some embodiments include an outer polymeric layer with a Shore hardness of from about 25 A to about 80 A, or from about 20 D to about 40 D. One particular embodiment comprises a readily available polyurethane with a Shore hardness of 72 Å. Another particular embodiment comprises a polyethylene inner polymeric layer dipped in polyurethane or silicone to create the outer polymeric layer.

The sheath 66 can also include a radiopaque filler or marker as described above. In some embodiments, a distinct radiopaque marker or band can be applied to some portion of the sheath 66. For example, a radiopaque marker can be coupled to the inner polymeric layer 68, the outer polymeric layer 70, and/or can be positioned in between the inner and outer polymeric layers 68, 70.

Figure 27A:
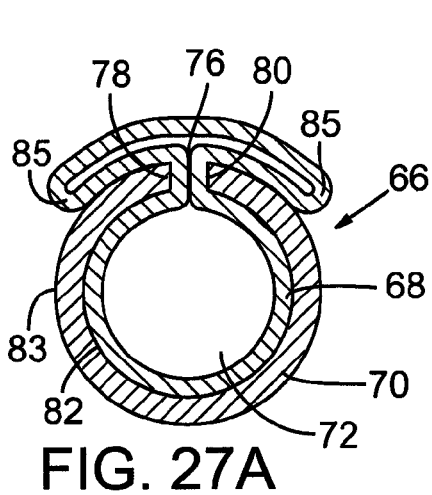
FIG. 27 illustrates a section view of one embodiment of a sheath, wherein the outer tubular layer contains a longitudinal cut, and the inner layer extends into the gap created by the cut in the outer tubular layer, in an unexpanded configuration.
Figure 28:
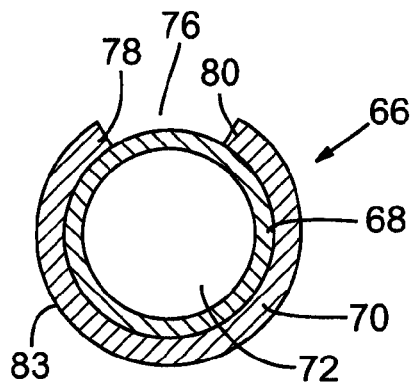
FIG. 28 shows a section view of the sheath of FIG. 27 in an expanded configuration.

FIGS. 27A-27E and 28 illustrate section views of various embodiments of unexpanded (FIGS. 27A-27E) and expanded (FIG. 28) sheaths 66 according to the present disclosure. The sheath 66 includes a split outer polymeric tubular layer 70 having a longitudinal cut 76 through the thickness of the outer polymeric tubular layer 70 such that the outer polymeric tubular layer 70 comprises a first portion 78 and a second portion 80 separable from one another along the cut 76. An expandable inner polymeric layer 68 is associated with an inner surface 82 of the outer polymeric tubular layer 70, and, in the unexpanded configuration shown in FIG. 27, a portion of the inner polymeric layer 68 extends through a gap created by the cut 76 and can be compressed between the first and second portions 78, 80 of the outer polymeric tubular layer 70. Upon expansion of the sheath 66, as shown in FIG. 28, first and second portions 78, 80 of the outer polymeric tubular layer 70 have separated from one another, and the inner polymeric layer 68 is expanded to a substantially cylindrical tube. In some embodiments, two or more longitudinal cuts 76 may be provided through the thickness of the outer polymeric tubular layer 70. In such embodiments, a portion of the inner polymeric layer 68 may extend through each of the longitudinal cuts 76 provided in the outer polymeric tubular layer 70.

Figure 27B:
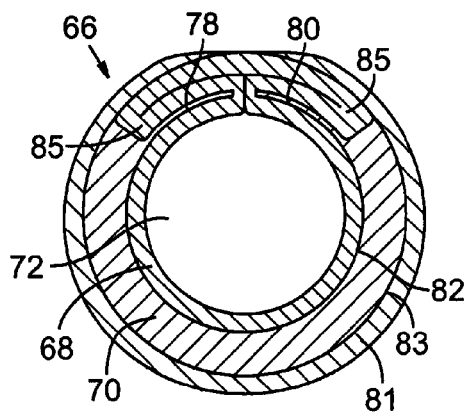
Figure 27C:
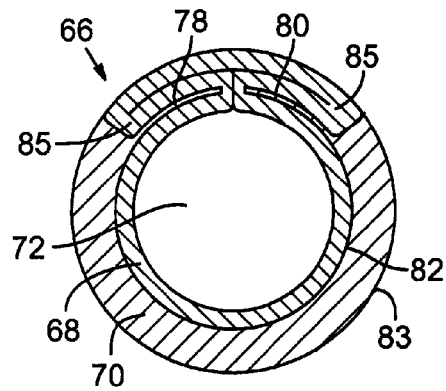
Figure 27D:
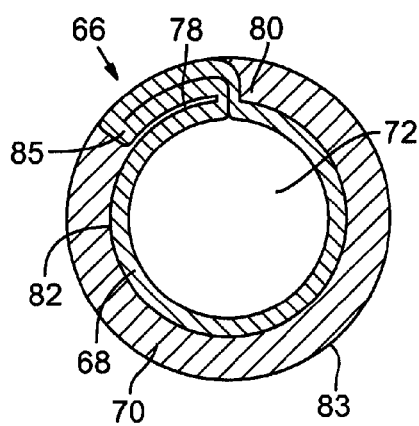
Figure 27E:
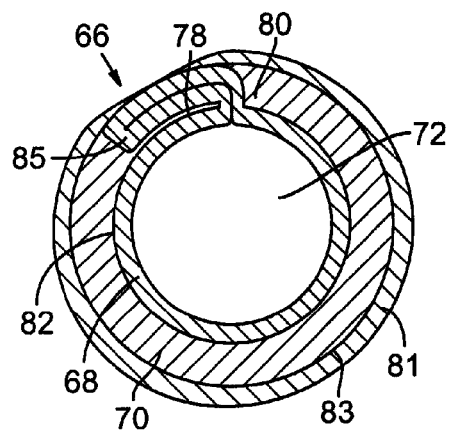

Preferably, the inner polymeric layer 68 comprises one or more materials that are elastic and amenable to folding and/or pleating. For example, FIG. 27A illustrates an inner polymeric layer 68 with folded regions 85. As seen in FIGS. 27A-27E, the sheath 66 can be provided with one or more folded regions 85. Such folded regions 85 can be provided along a radial direction and substantially conform to the circumference of the outer polymeric tubular layer 70. At least a portion of the folded regions 85 can be positioned adjacent the outer surface 83 of the outer polymeric tubular layer 70. Additionally, as shown in FIGS. 27B and 27E, at least a portion of the folded region or regions 85 can be overlapped by an outer covering, such as outer polymeric covering 81. The outer polymeric covering 81 can be adjacent at least a portion of the outer surface 83 of the outer polymeric tubular layer 70. The outer polymeric covering 81 serves to at least partially contain the folded regions 85 of the inner polymeric layer 68, and can also prevent the folded regions 85 from separating from the outer polymeric tubular layer 70 when, for example, the sheath 66 undergoes bending. In some embodiments, the outer polymeric covering 81 can be at least partially adhered to the outer surface 83 of the outer polymeric tubular layer 70. The outer polymeric covering 81 can also increase the stiffness and/or durability of the sheath 66. Additionally, as shown in FIGS. 27B and 27E, the outer polymeric covering 81 may not entirely overlap the circumference of the sheath 66. For example, the outer polymeric covering 81 may be provided with first and second ends, where the ends do not contact one another. In these embodiments, only a portion of the folded region 85 of the inner polymeric layer 68 is overlapped by the outer polymeric covering 81.

In embodiments having a plurality of folded regions 85, the regions can be equally displaced from each other around the circumference of the outer polymeric tubular layer 70. Alternatively, the folded regions can be off-center, different sizes, and/or randomly spaced apart from each other. While portions of the inner polymeric layer 68 and the outer tubular layer 70 can be adhered or otherwise coupled to one another, the folded regions 85 preferably are not adhered or coupled to the outer tubular layer 70. For example, adhesion between the inner polymeric layer 68 and the outer tubular layer 70 can be highest in areas of minimal expansion.

One particular embodiment of the sheath illustrated in FIGS. 27-28 comprises a polyethylene (e.g. high density polyethylene) outer polymeric tubular layer 70 and a PTFE inner polymeric layer 68. However, other materials are suitable for each layer, as described above. Generally, suitable materials for use with the outer polymeric tubular layer 70 include materials having a high stiffness or modulus of strength that can support expansion and contraction of the inner polymeric layer 68.

In some embodiments, the outer polymeric tubular layer 70 comprises the same material or combination of materials along the entire length of the outer polymeric tubular layer 70. In alternative embodiments, the material composition can change along the length of the outer polymeric tubular layer 70. For example, the outer polymeric tubular layer can be provided with one or more segments, where the composition changes from segment to segment. In one particular embodiment, the Durometer rating of the composition changes along the length of the outer polymeric tubular layer 70 such that segments near the proximal end comprise a stiffer material or combination of materials, while segments near the distal end comprise a softer material or combination of materials. This can allow for a sheath 66 having a relatively stiff proximal end at the point of introducing a delivery apparatus, while still having a relatively soft distal tip at the point of entry into the patient's vessel.

As with other disclosed embodiments, the embodiments of sheath 66 shown in FIGS. 27-28 can be provided in a wide range of sizes and dimensions. For example, the sheath 66 can be provided with an unexpanded inner diameter of from about 3 Fr to about 26 Fr. In some embodiments, the sheath 66 has an unexpanded inner diameter of from about 15 Fr to about 16 Fr. In some embodiments, the unexpanded inner diameter of the sheath 66 can range from about 3 Fr to about 26 Fr at or near the distal end of sheath 66, while the unexpanded inner diameter of the sheath 66 can range from about 3 Fr to about 28 Fr at or near the proximal end of sheath 66. For example, in one unexpanded embodiment, the sheath 66 can transition from an unexpanded inner diameter of about 16 Fr at or near the distal end of the sheath 66 to an unexpanded inner diameter of about 26 Fr at or near the proximal end of the sheath 66.

The sheath 66 can be provided with an unexpanded outer diameter of from about 3 Fr to about 30 Fr, and, in some embodiments has an unexpanded outer diameter of from about 18 Fr to about 19 Fr. In some embodiments, the unexpanded outer diameter of the sheath 66 can range from about 3 Fr to about 28 Fr at or near the distal end of sheath 66, while the unexpanded outer diameter of the sheath 66 can range from about 3 Fr to about 30 Fr at or near the proximal end of sheath 66. For example, in one unexpanded embodiment, the sheath 66 can transition from an unexpanded outer diameter of about 18 Fr at or near the distal end of the sheath 66 to an unexpanded outer diameter of about 28 Fr at or near the proximal end of the sheath 66.

The thickness of the inner polymeric layer 68 can vary, but in some preferred embodiments is from about 0.002 inches to about 0.015 inches. In some embodiments, expansion of the sheath 66 can result in expansion of the unexpanded outer diameter of from about 10% or less to about 430% or more.

As with other illustrated and described embodiments, the embodiments shown in FIGS. 27-28 can be provided with a radiopaque filler and/or a radiopaque tip marker as described above. The sheath 66 can be provided with a radiopaque tip marker provided at or near the distal tip of the sheath 66. Such a radiopaque tip marker can comprise materials such as those suitable for the radiopaque filler, platinum, iridium, platinum/iridium alloys, stainless steel, other biocompatible metals, or combinations thereof.

Figure 29A:
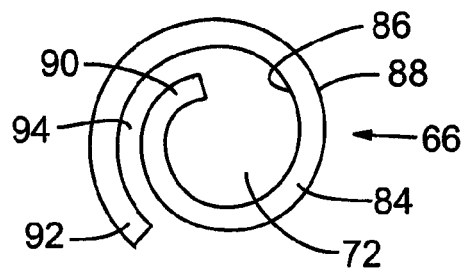
FIGS. 29A-29D show section views of various embodiments of a sheath having overlapping sections.
Figure 29B:
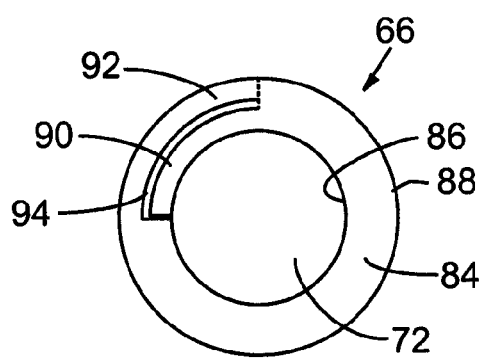
Figure 29C:
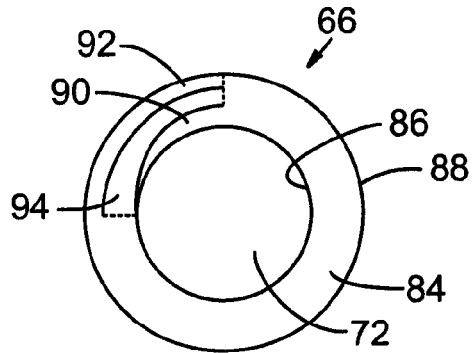
Figure 29D:
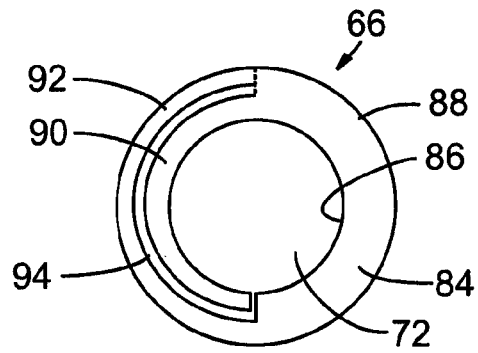

FIGS. 29A-29D show section views of other possible configurations of a sheath 66 for introducing a prosthetic device into a patient's vasculature. The sheath 66 comprises a polymeric tubular layer 84 having an inner surface 86 and an outer surface 88. The thickness of the polymeric tubular layer 84 extends from the inner surface 86 to the outer surface 88. As shown in FIGS. 29B-29D, the polymeric tubular layer 84 can be formed with at least a first angular portion 90 of reduced thickness adjacent the inner surface 86 and a second angular portion 92 of reduced thickness adjacent the outer surface 88, with the second portion 92 at least partially overlapping the first portion 90. FIG. 29A illustrates a similar configuration, where a second portion 92 at least partially overlaps a first portion 90 in a partial coil configuration. In the embodiment of FIG. 29A, the second portion 92 and the first portion 90 can have the same thickness.

In preferred embodiments, the first and second portions 90, 92 are not adhered to one another. In some embodiments, and best seen in FIG. 29A, there can be a small gap 94 between the first and second portions 90, 92 that can give the sheath 66 the appearance of having two interior lumens 72, 94. FIGS. 29A-29D illustrate the sheath 66 in unexpanded configurations. Preferably, upon expansion of the sheath 66, the ends of the first and second portions 90, 92 abut or are in close proximity to each other to reduce or eliminate any gap between them.

Figure 33:
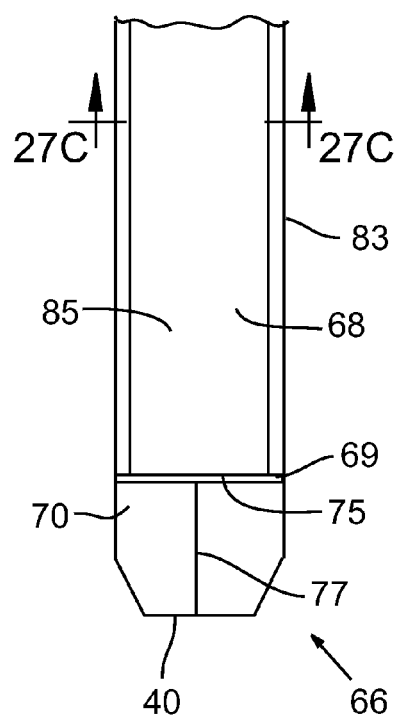
FIG. 33 illustrates a plan view of one embodiment of a sheath having a partial slit or score line.

In some embodiments, a sheath 66 can comprise a partial slit or score line along at least a portion of its length. For example, as shown in FIG. 33, a sheath 66 can comprise an outer polymeric tubular layer 70 over an inner polymeric layer 68. The inner polymeric layer can extend through a cut in the outer polymeric tubular layer 70, to form a folded region 85 on the outer surface of the outer polymeric tubular layer 70, such as also shown in FIG. 27C. The folded region 85 of the inner layer, in some embodiments, terminates before the outer polymeric tubular layer 70 (i.e. the outer polymeric tubular layer 70 is longer than the inner layer). As shown in FIG. 33, in these embodiments, the sheath 66 can comprise a partial slit or score line 77 that can extend from the termination (distal end) 75 of the folded region 85 to the distal end 40 of the sheath 66. In some embodiments, score line 77 can facilitate expansion of the sheath 66.

Figure 34:
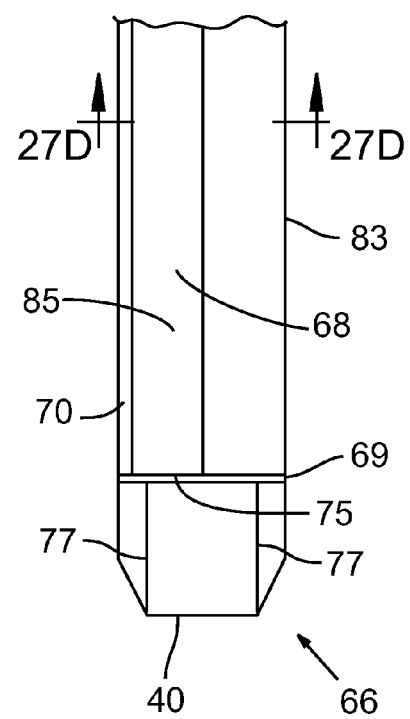
FIG. 34 illustrates a plan view of another embodiment of a sheath having a partial slit or score line.

Score line 77 can be substantially centrally located with respect to the folded region 85. In alternative embodiments, score line 77 can be positioned in other locations relative to the folded region 85. Also, sheath 66 can comprise one or more score lines 77. For example, as shown in FIG. 34, one or more score lines 77 can be peripherally located with respect to the folded region 85. The one or more score lines 77 can be positioned anywhere around the circumference of the outer polymeric tubular layer 70. In embodiments comprising a radiopaque marker 69 as seen in FIG. 33, a score line 77 can extend from, for example, the distal end of the radiopaque marker 69 substantially to the distal end 40 of the sheath 66.

FIGS. 35 and 36 illustrate an expandable sheath 100 according to the present disclosure, which can be used with a delivery apparatus for delivering a prosthetic device, such as a tissue heart valve into a patient. In general, the delivery apparatus can include a steerable guide catheter (also referred to as a flex catheter), a balloon catheter extending through the guide catheter, and a nose catheter extending through the balloon catheter (e.g., as depicted in FIG. 1). The guide catheter, the balloon catheter, and the nose catheter can be adapted to slide longitudinally relative to each other to facilitate delivery and positioning of the valve at an implantation site in a patient's body. However, it should be noted that the sheath 100 can be used with any type of elongated delivery apparatus used for implanting balloon-expandable prosthetic valves, self-expanding prosthetic valves, and other prosthetic devices. Generally, sheath 100 can be inserted into a vessel (e.g., the femoral or iliac arteries) by passing through the skin of patient, such that a soft tip portion 102 at the distal end 104 of the sheath 100 is inserted into the vessel. The sheath 100 can also include a proximal flared end portion 114 to facilitate mating with an introducer housing 101 and catheters mentioned above (e.g., the proximal flared end portion 114 can provide a compression fit over the housing tip and/or the proximal flared end portion 114 can be secured to the housing 101 via a nut or other fastening device or by bonding the proximal end of the sheath to the housing). The introducer housing 101 can house one or more valves that form a seal around the outer surface of the delivery apparatus once inserted through the housing, as known in the art. The delivery apparatus can be inserted into and through the sheath 100, allowing the prosthetic device to be advanced through the patient's vasculature and implanted within the patient.

Sheath 100 can include a plurality of layers. For example, sheath 100 can include an inner layer 108 and an outer layer 110 disposed around the inner layer 108. The inner layer 108 can define a lumen through which a delivery apparatus can travel into a patient's vessel in order to deliver, remove, repair, and/or replace a prosthetic device, moving in a direction along the longitudinal axis X. As the prosthetic device passes through the sheath 100, the sheath locally expands from a first, resting diameter to a second, expanded diameter to accommodate the prosthetic device. After the prosthetic device passes through a particular location of the sheath 100, each successive expanded portion or segment of the sheath 100 at least partially returns to the smaller, resting diameter. In this manner, the sheath 100 can be considered self-expanding, in that it does not require use of a balloon, dilator, and/or obturator to expand.

The inner and outer layers 108, 110 can comprise any suitable materials. Suitable materials for the inner layer 108 include polytetrafluoroethylene (PTFE), ethylene tetrafluoroethylene (ETFE), nylon, polyethylene, polyether block amide (e.g., Pebax), and/or combinations thereof. In one specific embodiment the inner layer 108 can comprise a lubricious, low-friction, or hydrophilic material, such as PTFE. Such low coefficient of friction materials can facilitate passage of the prosthetic device through the lumen defined by the inner layer 108. In some embodiments, the inner layer 108 can have a coefficient of friction of less than about 0.1. Some embodiments of a sheath 100 can include a lubricious liner on the inner surface of the inner layer 108. Examples of suitable lubricious liners include materials that can further reduce the coefficient of friction of the inner layer 108, such as PTFE, polyethylene, polyvinylidine fluoride, and combinations thereof. Suitable materials for a lubricious liner also include other materials desirably having a coefficient of friction of about 0.1 or less.

Suitable materials for the outer layer 110 include nylon, polyethylene, Pebax, HDPE, polyurethanes (e.g., Tecoflex), and other medical grade materials. In one embodiment, the outer layer 110 can comprise high density polyethylene (HDPE) and Tecoflex (or other polyurethane material) extruded as a composite. In some embodiments, the Tecoflex can act as an adhesive between the inner layer 108 and the outer layer 110 and may only be present along a portion of the inner surface of the outer layer 110. Other suitable materials for the inner and outer layers are also disclosed in U.S. Patent Application Publication No. 2010/0094392, which is incorporated herein by reference.

Additionally, some embodiments of a sheath 100 can include an exterior hydrophilic coating on the outer surface of the outer layer 110. Such a hydrophilic coating can facilitate insertion of the sheath 100 into a patient's vessel. Examples of suitable hydrophilic coatings include the Harmony™ Advanced Lubricity Coatings and other Advanced Hydrophilic Coatings available from SurModics, Inc., Eden Prairie, Minn. DSM medical coatings (available from Koninklijke DSM N. V, Heerlen, the Netherlands), as well as other hydrophilic coatings (e.g., PTFE, polyethylene, polyvinylidine fluoride), are also suitable for use with the sheath 100.

Best seen in FIG. 36, the soft tip portion 102 can comprise, in some embodiments, low density polyethylene (LDPE) and can be configured to minimize trauma or damage to the patient's vessels as the sheath is navigated through the vasculature. For example, in some embodiments, the soft tip portion 102 can be slightly tapered to facilitate passage through the vessels. The soft tip portion 102 can be secured to the distal end 104 of the sheath 100, such as by thermally bonding the soft tip portion 102 to the inner and outer layers of the sheath 100. Such a soft tip portion 102 can be provided with a lower hardness than the other portions of the sheath 100. In some embodiments, the soft tip 102 can have a Shore hardness from about 25 D to about 40 D. The tip portion 102 is configured to be radially expandable to allow a prosthetic device to pass through the distal opening of the sheath 100. For example, the tip portion 102 can be formed with a weakened portion, such as an axially extending score line or perforated line that is configured to split and allow the tip portion to expand radially when the prosthetic device passes through the tip portion (such as shown in the embodiments of FIGS. 33 and 34).

Figure 37:
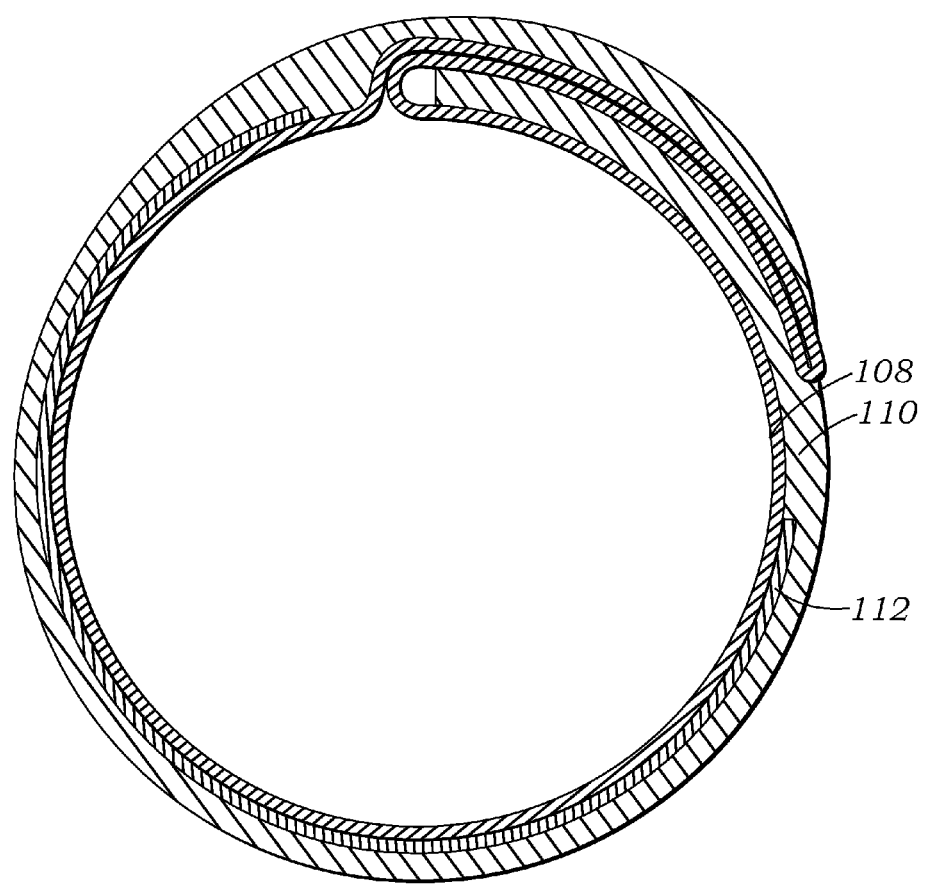
FIG. 37 is a section view of the distal end of the sheath of FIG. 35, taken along line 37-37 in FIG. 36.

FIG. 37 shows a cross-section view of the sheath 100 taken near the distal end 104 of the sheath 100. As shown in FIGS. 36 and 37, the sheath 100 can include at least one radiopaque filler or marker, such as a discontinuous, or C-shaped, band 112 positioned near the distal end 104 of the sheath 100. The marker 112 can be associated with the inner and/or outer layers 108, 110 of the sheath 100. For example, as shown in FIG. 37, the marker 112 can be positioned between the inner layer 108 and the outer layer 110. In alternative embodiments, the marker 112 can be associated with the outer surface of the outer layer 110. In some embodiments, the marker 112 can be embedded or blended within the inner or outer layers 108, 110.

The C-shaped band 112 can serve as a radiopaque marker or filler, to enable visibility of the sheath 100 under fluoroscopy during use within a patient. The C-shaped band 112 can comprise any suitable radiopaque material, such as barium sulfite, bismuth trioxide, titanium dioxide, bismuth subcarbonate, platinum, iridium, and combinations thereof. In one specific embodiment, the C-shaped band can comprise 90% platinum and 10% iridium. In other embodiments, the marker 112 need not be a C-shaped band. Other shapes, designs, and configurations are possible. For example, in some embodiments, the marker 112 can extend around the entire circumference of the sheath 100. In other embodiments, the marker 112 can comprise a plurality of small markers spaced around the sheath 100.

Figure 38:
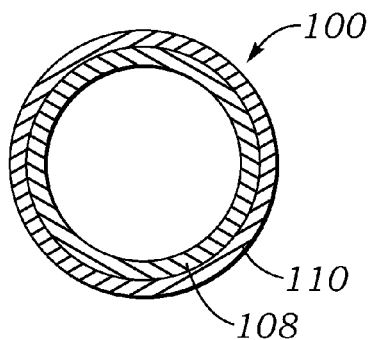
FIG. 38 is a section view of a proximal section of the sheath of FIG. 35, taken along line 38-38 in FIG. 35.
Figure 39:
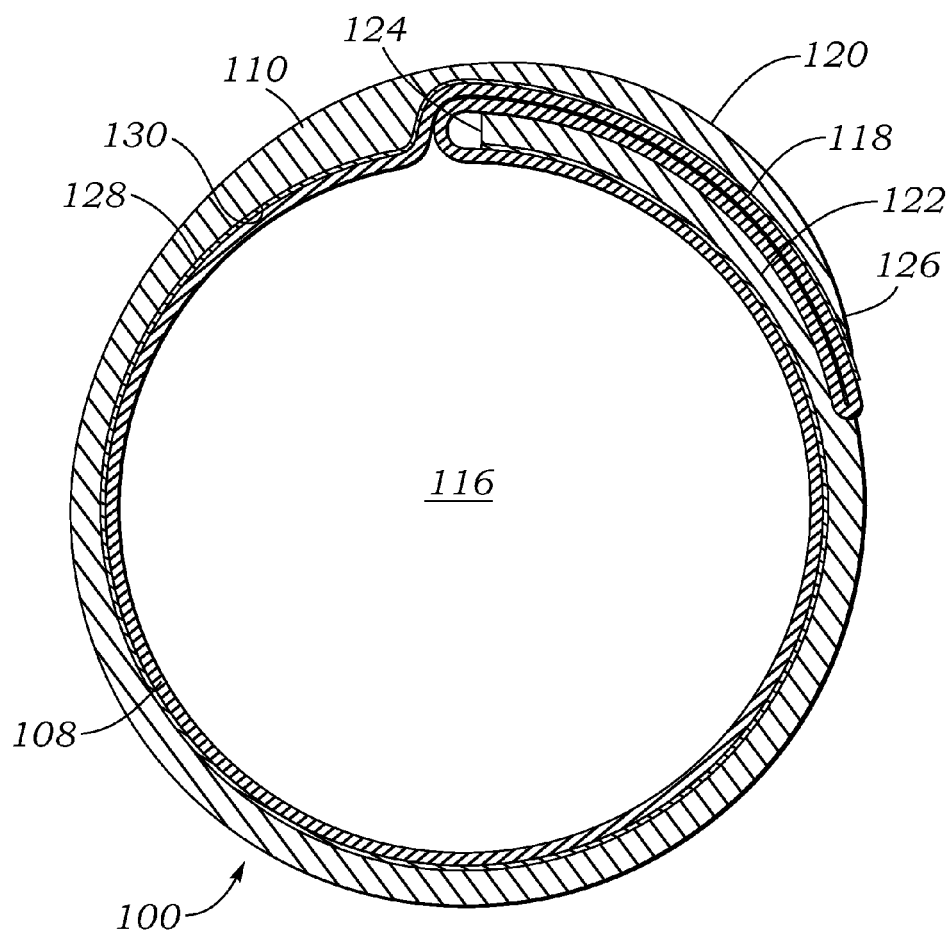
FIG. 39 is a section view of the sheath of FIG. 35 in a rest (unexpanded) configuration, taken along line 39-39 in FIG. 35.

FIGS. 38 and 39 show additional cross sections taken at different points along the sheath 100. FIG. 38 shows a cross-section of a segment of the sheath near the proximal end 106 of the sheath 100, as indicated by line 38-38 in FIG. 35. The sheath 100 at this location can include inner layer 108 and outer layer 110. At this location, near the proximal end of the sheath, the layers 108, 110 can be substantially tubular, without any slits or folded portions in the layers. By contrast, the layers 108, 110 at different locations along the sheath 100 (e.g., at the point indicated by line 39-39 in FIG. 35) can have a different configuration.

As shown in FIG. 39, the inner layer 108 can be arranged to form a substantially cylindrical lumen 116 therethrough. Inner layer 108 can include one or more folded portions 118. In the embodiment shown in FIG. 39, inner layer 108 is arranged to have one folded portion 118 that can be positioned on either side of the inner layer 108. Inner layer 108 can be continuous, in that there are no breaks, slits, or perforations in inner layer 108. Outer layer 110 can be arranged in an overlapping fashion such that an overlapping portion 120 overlaps at least a part of the folded portion 118 of the inner layer 108. As shown in FIG. 39, the overlapping portion 120 also overlaps an underlying portion 122 of the outer layer 110. The underlying portion 122 can be positioned to underlie both the overlapping portion 120 of the outer layer 110, as well as the folded portion 118 of the inner layer 108. Thus, the outer layer 110 can be discontinuous, in that it includes a slit or a cut in order to form the overlapping and underlying portions 120, 122. In other words, a first edge 124 of the outer layer 110 is spaced apart from a second edge 126 of the outer layer 110 so as not to form a continuous layer.

As shown in FIG. 39, the sheath 100 can also include a thin layer of bonding or adhesive material 128 positioned between the inner and outer layers 108, 110. In one embodiment, the adhesive material 128 can comprise a polyurethane material such as Tecoflex. The adhesive material 128 can be positioned on an inner surface 130 of at least a portion of the outer layer 110 so as to provide adhesion between selected portions of the inner and outer layers 108, 110. For example, the outer layer 110 may only include a Tecoflex layer 128 around the portion of the inner surface 130 that faces the lumen-forming portion of the inner layer 108. In other words, the Tecoflex layer 128 can be positioned so that it does not contact the folded portion 118 of the inner layer 108 in some embodiments. In other embodiments, the Tecoflex layer 128 can be positioned in different configurations as desired for the particular application. For example, as shown in FIG. 39, the Tecoflex layer 128 can be positioned along the entire inner surface 130 of the outer layer 110. In an alternative embodiment, the Tecoflex layer can be applied to the outer surface of the inner liner 108 instead of the inner surface of the outer layer. The Tecoflex layer can be applied to all or selected portions on the inner layer; for example, the Tecoflex layer can be formed only on the portion of the inner layer that faces the lumen-forming portion of the outer layer and not on the folded portion. The configuration of FIG. 39 allows for radial expansion of the sheath 100 as an outwardly directed radial force is applied from within (e.g., by passing a medical device such as a prosthetic heart valve through the lumen 116). As radial force is applied, the folded portion 118 can at least partially separate, straighten, and/or unfold, and/or the overlapping portion 120 and the underlying portion 122 of the outer layer 110 can slide circumferentially with respect to one another, thereby allowing the diameter of lumen 116 to enlarge.

Figure 40:
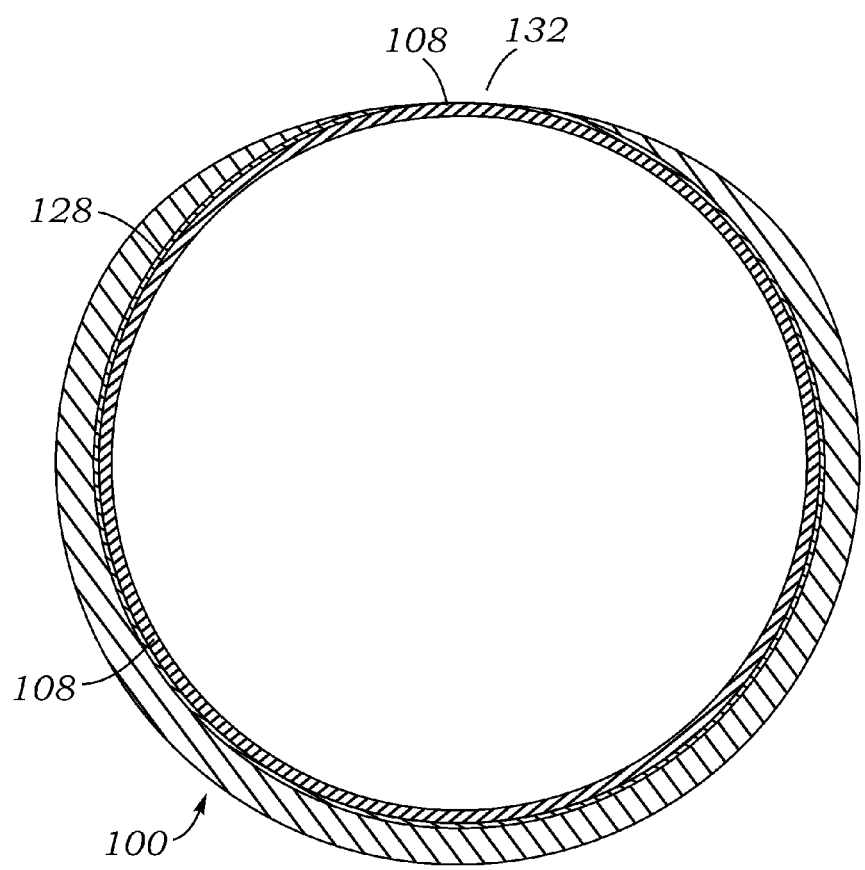
FIG. 40 is the section view of the sheath of FIG. 39, in an expanded configuration.

In this manner, the sheath 100 is configured to expand from a resting configuration (FIG. 39) to an expanded configuration shown in FIG. 40. In the expanded configuration, as shown in FIG. 40, an annular gap 132 can form between the longitudinal edges of the overlapping portion 120 and the underlying portion 122 of the outer layer 110. As the sheath 100 expands at a particular location, the overlapping portion 120 of the outer layer 110 can move circumferentially with respect to the underlying portion 122 as the folded portion 118 of the inner layer 108 unfolds. This movement can be facilitated by the use of a low-friction material for inner layer 108, such as PTFE. Further, the folded portion 118 can at least partially separate and/or unfold to accommodate a medical device having a diameter larger than that of lumen 116 in the resting configuration. As shown in FIG. 40, in some embodiments, the folded portion of the inner layer 108 can completely unfold, so that the inner layer 108 forms a cylindrical tube at the location of the expanded configuration.

The sheath 100 can be configured such that it locally expands at a particular location corresponding to the location of the medical device along the length of the lumen 116, and then locally contracts once the medical device has passed that particular location. Thus, a bulge may be visible, traveling longitudinally along the length of the sheath as a medical device is introduced through the sheath, representing continuous local expansion and contraction as the device travels the length of the sheath 100. In some embodiments, each segment of the sheath 100 can locally contract after removal of any radial outward force such that it regains the original resting diameter of lumen 116. In some embodiments, each segment of the sheath 100 can locally contract after removal of any radial outward force such that it at least partially returns to the original resting diameter of lumen 116.

The layers 108, 110 of sheath 100 can be configured as shown in FIG. 39 along at least a portion of the length of the sheath 100. In some embodiments, the layers 108, 110 can be configured as shown in FIG. 39 along the length A (FIG. 35) extending from a location adjacent the soft tip portion 102 to a location closer to the proximal end 106 of the sheath 100. In this matter, the sheath is expandable and contractable only along a portion of the length of the sheath corresponding to length A (which typically corresponds to the section of the sheath inserted into the narrowest section of the patient's vasculature).

FIGS. 41-49 illustrate additional embodiments and variations on the general sheath 100 described above. It is to be understood that the variations (e.g., materials and alternate configurations) described above with reference to FIGS. 35-40 can also apply to the embodiments shown in FIGS. 41-49. Furthermore, the variations described below with reference to FIGS. 41-49 can also be applied to the sheath described in FIGS. 35-40.

FIGS. 41-43 illustrate a sheath 700 that additionally includes a strain relief cover, also referred to as an elastic outer cover, or an elastic cover 702 positioned around at least a part of an inner layer 704 and outer layer 706. As shown in FIG. 41, the elastic cover 702 can extend for a length L along at least a portion of the main body of the sheath 700. In some embodiments, the elastic cover 702 can extend from the proximal end 708 of the sheath 700 and towards the distal end 709 of the sheath. In some embodiments, the elastic cover 702 extends only part way down the length of the sheath 700. In alternate embodiments, the elastic cover 702 can extend to a point adjacent the distal end 709, or can extend all the way to the distal end 709 of sheath 700. Furthermore, the elastic outer cover 702 need not extend all the way to the proximal end 708 of the sheath 700. In some embodiments, the elastic outer cover 702 may extend only part way towards the proximal end 708. In some embodiments, the longitudinal length L of the elastic cover 702 can range from about 10 cm to the entire length of the sheath 700.

As shown in FIGS. 42 and 43, the elastic cover 702 can be a continuous tubular layer, without slits or other discontinuities. The elastic cover 702 can be positioned to surround the entire circumference of outer layer 706, and can extend longitudinally along any portion of the length of the sheath 700. The elastic outer cover 702 can comprise any pliable, elastic material(s) that expand and contract, preferably with a high expansion ratio. Preferably, the materials used can include low durometer polymers with high elasticity, such as Pebax, polyurethane, silicone, and/or polyisoprene. Materials for the elastic outer cover 702 can be selected such that it does not impede expansion of the sheath 700. In fact, the elastic outer cover 702 can stretch and expand as the sheath 700 expands, such as by movement of the folded or scored inner liner with respect to itself.

The elastic outer cover 702 can, in some embodiments, provide hemostasis (e.g., prevent blood loss during implantation of the prosthetic device). For example, the elastic outer cover 702 can be sized or configured to form a seal with the patient's artery when inserted, such that blood is substantially prevented from flowing between the elastic outer cover 702 and the vessel wall. The elastic outer cover 702 can be inserted such that it passes the arteriotomy. For example, in embodiments where the elastic outer cover 702 does not extend all the way to the distal end 709 of the sheath 700, the elastic cover 702 can extend distally far enough such that when the sheath 700 is fully inserted into the patient, at least part of the elastic outer cover extends through the ateriotomoy site.

The elastic outer cover can have a thickness ranging from, for example, about 0.001" to about 0.010." In some embodiments, the outer cover can have a thickness of from about 0.003" to about 0.006." The elastic outer over can be configured to expand as the sheath expands, as shown in the expanded configuration in FIG. 43.

FIG. 42 shows a cross-section of the sheath 700 in a resting configuration having an inner diameter $D_1$. FIG. 43 shows a cross-section of the sheath 700 in an expanded configuration, having an inner diameter $D_2$, where $D_2$ is greater than $D_1$. Similar to the embodiment of FIGS. 35-40, the sheath 700 can include an inner layer 704 having a folded portion 710, and an outer layer 706 having an overlapping portion 712 and an underlying portion 714. The overlapping portion 712 overlaps at least a portion of the folded portion 710 of the inner layer, and the underlying portion 714 underlies at least a portion of the folded portion 710. As shown in FIGS. 42-43, in some embodiments, the overlapping portion 712 does not overlap the entire folded portion 710 of the inner layer 704, and thus a portion of the folded portion 710 can be directly adjacent to the elastic outer cover 702 in locations where the elastic cover 702 is present. In locations where the elastic cover 702 is not present, part of the folded portion 710 may be visible from the outside of the sheath 700, as seen in FIG. 41. In these embodiments, the sheath 700 can include a longitudinal seam 722 where the overlapping portion 712 terminates at the folded portion 710. In use, the sheath can be positioned such that the seam 722 is posterior to the point of the sheath that is 180 degrees from the seam 722 (e.g., facing downward in the view of FIG. 41). The seam 722 can also be seen in FIG. 41, which shows that the seam 722 need not extend the entire length of the sheath. In some embodiments, the proximal end portion of the sheath includes two layers without a folded portion (e.g., similar to FIG. 38) while the distal end portion of the sheath includes two layers with a folded portion (e.g., similar to FIG. 39). In some embodiments, the seam 722 can end at a transition point between portions of the sheath having a folded inner layer and portions of the sheath not having a folded inner layer.

In some embodiments, the folded portion 710 can include a weakened portion, such as a longitudinal perforation, score line, and/or slit 716 along at least a portion of the length of the inner layer 704. The slit 716 can allow for two adjacent ends 718, 720 of the folded portion 710 to move relative to one another as the sheath 700 expands to the expanded configuration shown in FIG. 43. As a device having an outer diameter device larger than the initial resting inner diameter of the sheath 700 is inserted through the sheath 700, the device can cause local expansion of the sheath 700 and cause the sheath 700 to expand at the partial score or split line location 716. The weakened portion 716 can extend longitudinally along any portion of the expandable sheath 700.

FIGS. 44 and 45 show another embodiment of an expandable sheath 800 having an initial diameter in a resting configuration (FIG. 44) and a larger expanded diameter in an expanded configuration (FIG. 45). The sheath 800 can include an elastic outer cover 802, an inner layer 804, and an outer layer 806. Inner layer 804 can include first and second folded portions 808, 810. The folded portions 808, 810 can be arranged such that they fold away from one another in opposite directions around the circumference of the sheath 800. For example, folded portion 808 can be folded to the right in the view of FIG. 44 and folded portion 810 can be folded to the left such that they do not overlap one another, but share a common segment 812 which is part of both folded portions 808, 810. In contrast to previous embodiments, the outer layer 806 does not include an overlapping portion in this embodiment, but rather has first and second underlying portions 814, 816, which underlie the first and second folded portions 808, 810, respectively. The inner layer 804 can extend through a gap between the ends of the adjacent underlying portions 814, 816 (e.g., between a first end and a second end of discontinuous outer layer 806).

Each folded portion 808, 810 can include a weakened portion 818, such as a slit, score line, and/or perforation. Weakened portion 818 can allow the expandable sheath 800 to expand easily without a high radial force. As the sheath 800 expands, segment 812 along the top of the folded portions 808, 810 of inner layer 804 can be configured to split apart from the rest of the folded portions 808, 810 and the first and second underlying portions 814, 816 can move away from one another so as to create an enlarged lumen within the inner layer 804. Weakened portions 818 can allow for the segment 812 to easily split apart from the inner layer 804 as the sheath 800 expands.

Figure 47:
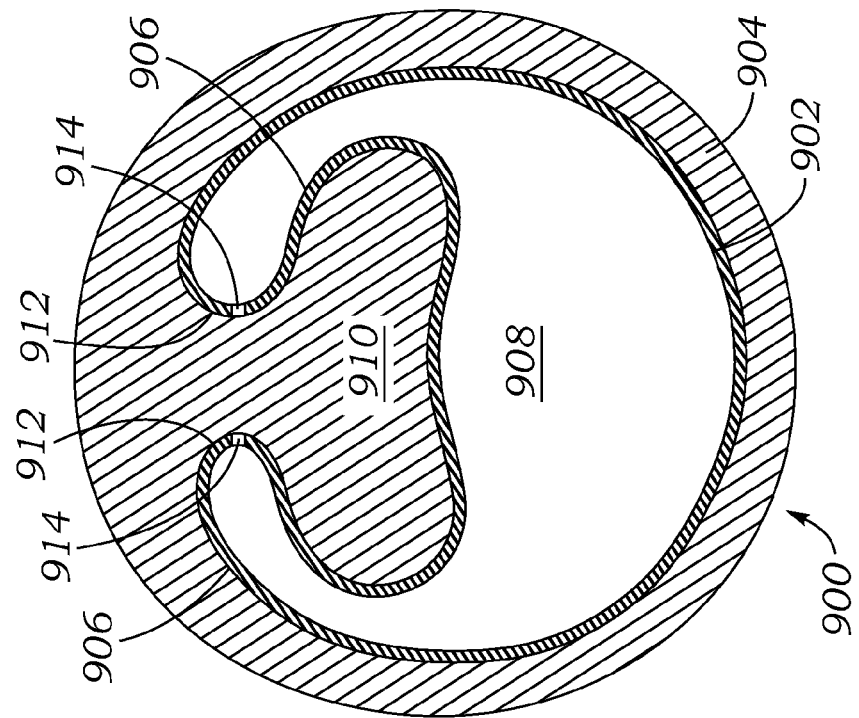
FIG. 47 shows an expanded configuration of the sheath of FIG. 46.
Figure 46:
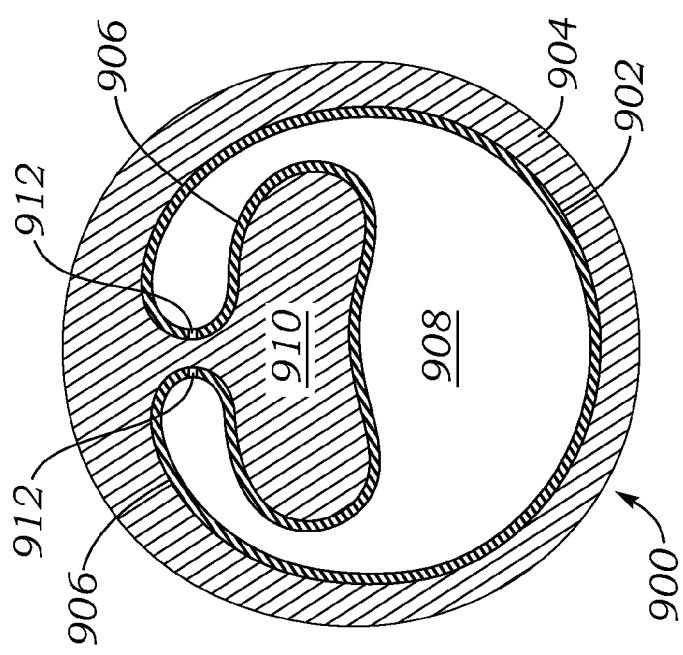
FIG. 46 illustrates a section view of another embodiment of an expandable sheath.

FIGS. 46-47 show another embodiment of an expandable sheath 900. Sheath 900 can be provided with an inner layer 902 and an elastic cover 904 surrounding the inner layer 902. While not shown, sheath 900 can additionally include an intermediate layer positioned between the inner layer 902 and the elastic cover 904. If present, the intermediate layer can closely follow the contour of the inner layer 902.

Inner layer 902 can be shaped to include one or more folded portions 906 arranged to form a generally horseshoe-shaped lumen 908 that extends longitudinally through sheath 900 along the inner surface of the inner layer 902. The folded portions 906 can be arranged to form an area 910 positioned with the lumen 908 and radially inward from the elastic cover 904. In some embodiments, the area 910 can include one or more voids (e.g., smaller lumens or openings extending through portion 910). In some embodiments, the area 910 can be filled with material (e.g., HDPE) reflowed from an intermediate layer while the sheath is being made. In some embodiments, the area 910 can be filled with material reflowed from the elastic cover 904 during the sheath manufacturing process.

The inner layer 902 can include one or more weakened portions 912, such as score lines, perforations, or slits. The weakened portions 912 can be configured to split apart, separate, or widen as the sheath expands from its initial resting configuration (FIG. 46) to an expanded configuration (FIG. 47) in the presence of a radial force. As the sheath 900 expands, material from the area 910 can cover any gaps 914 formed at the weakened portions 912, thereby keeping the lumen 908 substantially sealed.

FIG. 48 shows another embodiment of an expandable sheath 1000 having an inner layer 1002 and a discontinuous outer layer 1004. Sheath 1000 is similar to the sheath 800 of FIG. 44, except that sheath 1000 is shown without an elastic outer cover and further, the inner layer 1002 is continuous, without weakened portions at the folds 1006. As shown in FIG. 48, the inner layer 1002 can be configured to have one or more folds 1006 (e.g., two folds positioned on the outer surface of the outer layer 1004), with portions 1008 of the outer layer 1004 extending between the folds 1006 and the outer surface 1010 of the inner layer 1002 underlying the folds 1006.

FIG. 49 shows yet another embodiment of an expandable sheath 1100 having an inner layer 1102 and an outer layer 1104. The sheath 1100 is similar to the sheath 100 shown in FIG. 39 in that the inner layer 1102 can be continuous with a folded portion 1106, and the outer layer 1104 can be discontinuous with an overlapping portion 1108 overlapping at least a part of the folded portion 1106 and an underlying portion 1110 underlying at least a part of the folded portion 1106. The underlying portion 1110 can thus be positioned between an outer surface 1112 of the lumen-forming portion of the inner layer 1102 and the folded portion 1106.

The inner layers 1002, 1102 of the sheaths 1000, 1100, respectively, of FIGS. 48-49 can be optimized to perform slightly differently than the inner layers of sheaths described above. For example, different materials can be used for the inner liner to increase durability and softness of the seam (although such materials can also be used with the other embodiments of expandable sheaths described above). For example, materials such as woven fabrics or braid filaments can be used. Such fabrics, filaments, or yarns can comprise, for example, PTFE, PET, PEEK, and/or nylon yarns or filaments. These materials can advantageously provide a soft and flexible layer that can be easily formed into the desired shapes or folded portions. Additionally, such materials can withstand high temperatures, as well as can possess high tensile strength and tear resistance. Nonetheless, these materials can also be elastic, experience minimal kinking, and provide soft distal edges for less traumatic insertion into a patient's vessels.

Various methods can be used to produce the sheaths discussed above and below, throughout the present disclosure. For example, a method of making the sheath shown in FIGS. 2A-2D can comprise providing a mandrel and applying an inner layer on the mandrel, such as by spray coating or dip coating the mandrel. An intermediate layer, such as a mesh structure, can then be mounted on the inner layer. An outer layer can be applied over the intermediate layer, such as by a second spray coating or dip coating step. Methods can comprise etching or surface treating at least a portion of the inner layer. Also, methods can comprise providing one or more notches and/or cuts in the inner layer and/or the outer layer. Cuts and/or notches can be provided by, for example, laser cutting or etching one or more layers.

In some embodiments of methods of making a sheath such as the sheaths illustrated in FIGS. 2A-2D, layers can be pre-formed and mounted on a mandrel, and then fused or thermally bonded together. For example, in one method, an inner layer is applied to a mandrel. An intermediate layer can be applied to the outer surface of the inner layer. An outer layer can be applied to the outer surface of the intermediate layer. Heat shrink tubing can be applied, and the assembly heated, such that the inner layer, the intermediate layer, and/or the outer layer are thermally bonded and compressed together under the heat shrink tubing.

Figure 30:
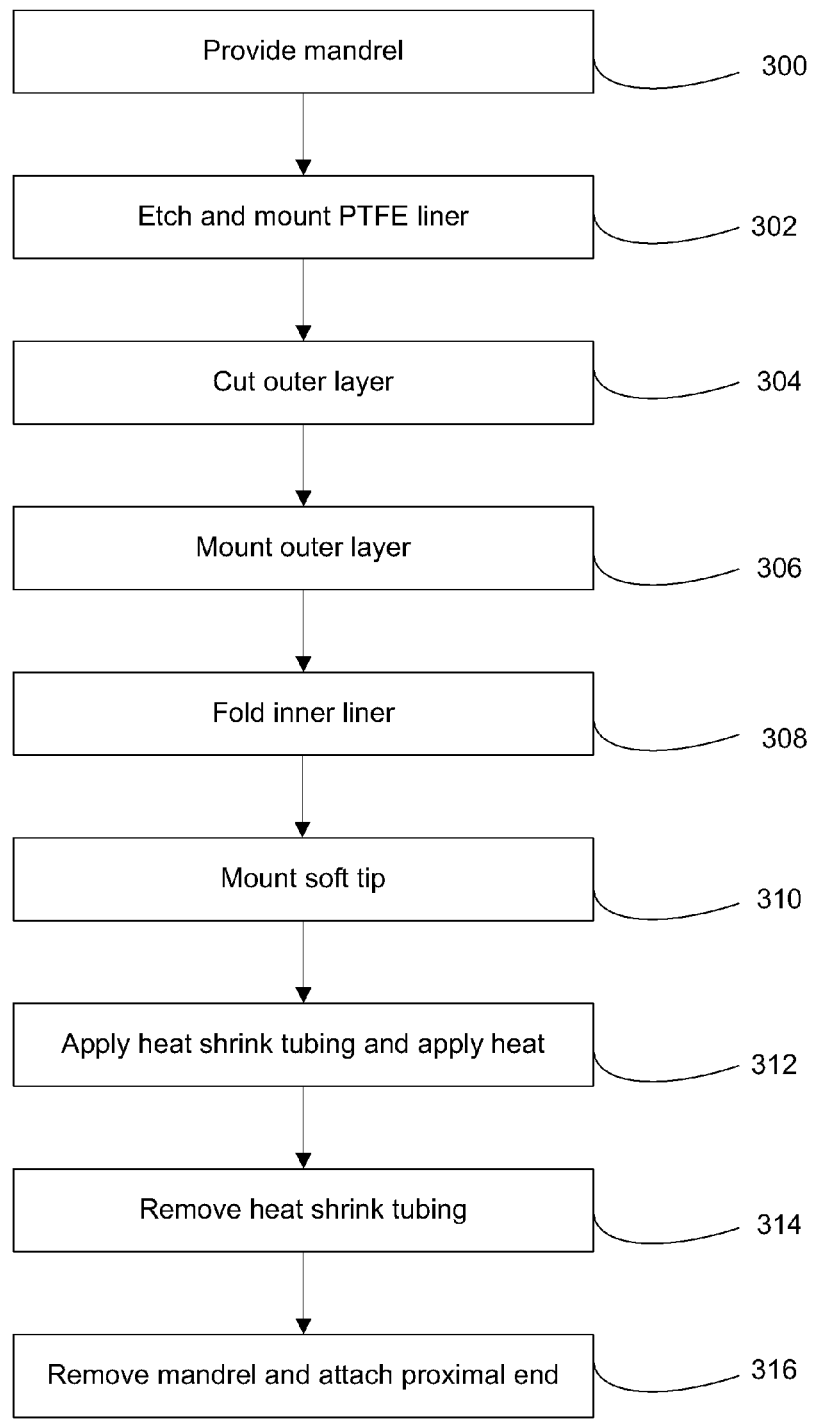
FIG. 30 illustrates a block diagram of one embodiment of a method of making a sheath according to the present disclosure.
Figure 32A:
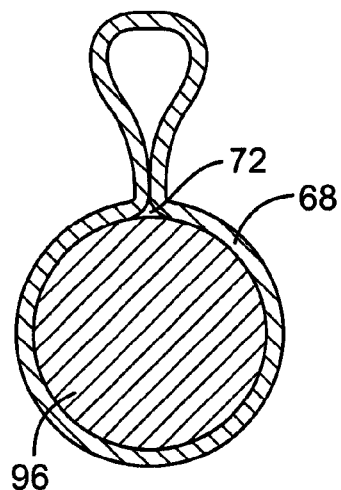

FIG. 30 illustrates a block diagram of one method of producing a sheath for use with a delivery apparatus in minimally invasive surgery. One or more mandrels can be provided (step 300). The mandrel can be provided with an exterior coating, such as a Teflon® coating, and the mandrel's diameter can be predetermined, based on the desired size of the resulting sheath. A liner that will become the inner polymeric layer of the sheath, such as a PTFE or high density polyethylene liner, can be mounted on the mandrel (step 302). The liner can be etched and/or surface treated prior to being mounted on the mandrel, according to conventional etching and surface treatment methods. FIG. 32A illustrates a section view of a sheath at steps 300 and 302 of FIG. 30. A coated mandrel 96 is inserted within the lumen 72 of the inner polymeric layer 68. The circumference of the inner polymeric layer 68 is larger than the circumference of the mandrel 96, such that an excess portion of the inner polymeric layer 68 can be gathered above the mandrel 96.

A layer of material that will become the outer polymeric tubular layer, such as a layer comprising polyurethane or polyolefin, can be cut or notched through all, substantially all, or a part of the thickness of the layer (step 304). Such a cut or notch can extend longitudinally along the length of the layer and can extend along substantially the entire length of the outer polymeric tubular layer. In alternative embodiments, the cut or notch can be provided along only a portion of the outer polymeric tubular layer. For example, the outer polymeric tubular layer can be cut starting at the distal end of the outer polymeric tubular layer, with the cut ending before the proximal end of the outer polymeric tubular layer. In one embodiment, the cut can end at a transition, where the outer diameter of the outer polymeric tubular layer increases or decreases. In one specific embodiment, the cut or notch can extend longitudinally along about 75% of the length of the sheath.

Figure 32B:
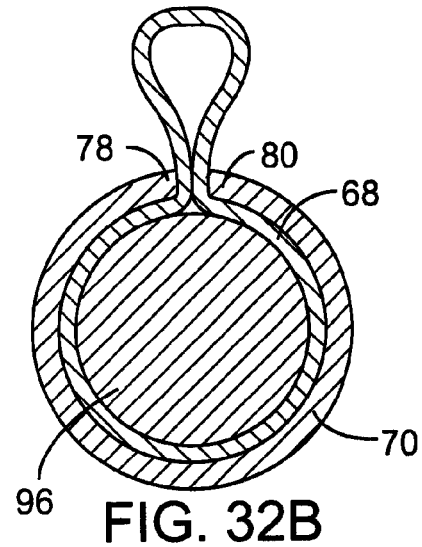

The cut or notched outer polymeric tubular layer can be applied, positioned, adhered, mounted, thermally fused or bonded, dip coated, and/or otherwise coupled to the etched inner liner (step 306). FIG. 32B shows a section view of the sheath at step 306 of FIG. 30, with outer polymeric tubular layer 70 applied to the inner polymeric layer 68 such that a portion of the inner polymeric layer 68 extends between the cut formed between first and second portions 78, 80 of the outer polymeric tubular layer 70.

Figure 32C:
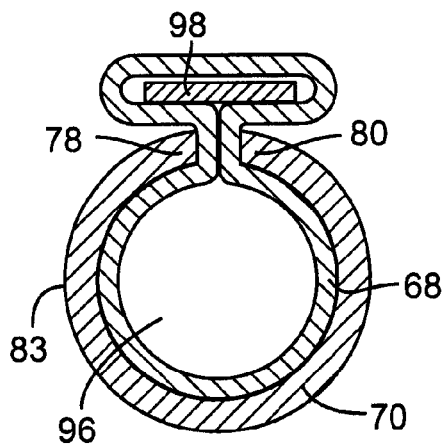
Figure 32D:
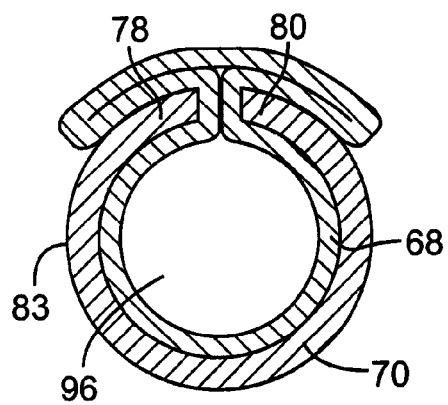
Figure 32E:
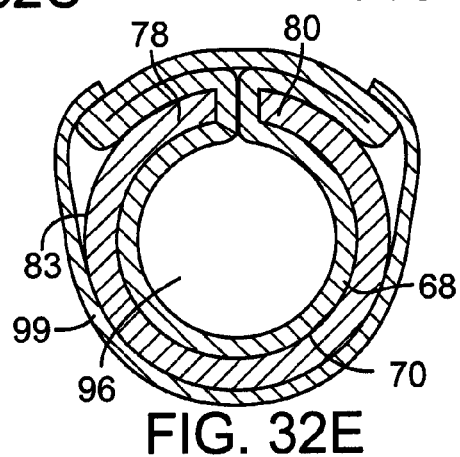

In alternative embodiments, the outer polymeric tubular layer can be notched or cut after being mounted on the inner liner/mandrel assembly. The outer polymeric tubular layer can optionally be provided with a hydrophilic coating and/or provided with additional layers, such as being dip coated with polyurethane. Some portion of the inner liner can protrude through the cut in the outer polymeric tubular layer after such outer polymeric tubular layer is mounted onto the inner liner/mandrel arrangement. Using, for example, a split tool, the protruding portion of the inner liner can be folded down onto the outer surface of the outer polymeric tubular layer (step 308). In some embodiments, the protruding portion of the inner liner is folded down along the entire length of the resulting sheath, while in other embodiments, the protruding portion of the inner liner is only present along a portion of the length of the sheath, or is only folded down along a portion of the length of the resulting sheath. FIG. 32C shows a section view of the sheath at step 308 of FIG. 30. A split tool 98 is used to fold the excess portion of inner polymeric layer 68 over a portion of the outer surface 83 of the outer polymeric tubular layer 70. FIG. 32D shows a section view of the sheath after completion of step 308 of FIG. 30. Split tool 98 has been removed, and folding of the excess portion of the inner polymeric layer 68 has been completed. FIG. 32E shows a section view of an outer covering, such as outer polymeric covering 99, that can be applied such that it overlaps a portion of the folded portion of inner polymeric layer 68. The outer polymeric covering 99 contacts at least a portion of the outer surface 83 of the outer polymeric tubular layer 70.

A soft, atraumatic tip can be provided at the distal end of the resulting sheath (step 310). Additional outer layers can also be applied, if desired. Then, a layer of heat shrink tubing, such as fluorinated ethylene propylene (FEP) heat shrink tubing, can be positioned over the entire assembly (step 312). An appropriate amount of heat is applied, thus shrinking the heat shrink tubing and compressing the layers of the sheath together, such that components of the sheath can be thermally bonded or fused together where desired. Once the components of the sheath have been bonded together, the heat shrink tubing can be removed (step 314). Finally, the proximal end of the sheath can be adhered or otherwise attached to a housing of a catheter assembly, and the sheath can be removed from the mandrel (step 316).

Figure 31:
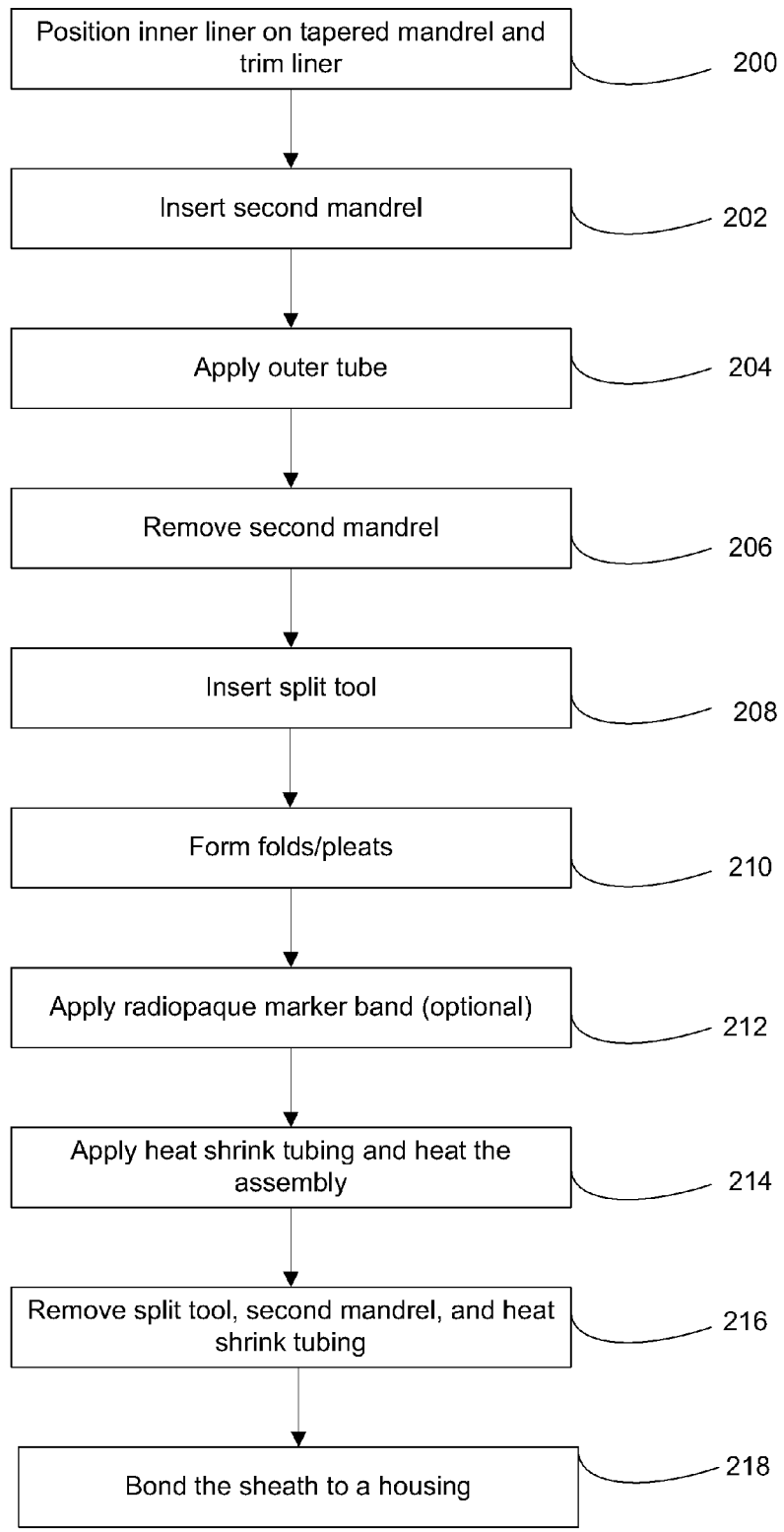
FIG. 31 illustrates a block diagram of another embodiment of a method of making a sheath according to the present disclosure.

FIG. 31 illustrates a block diagram of an alternative embodiment of a method of making a sheath. An inner liner, such as an etched PTFE tubing can be applied to a tapered mandrel, such as a 16 Fr tapered mandrel, and trimmed to an appropriate length (step 200). A second mandrel, such as a 0.070 inches diameter mandrel, can be inserted in the lumen of the inner liner such that the mandrels are arranged side by side in the inner liner (step 202). FIG. 32F shows a section view of a sheath at steps 200 and 202 of FIG. 31. An inner liner or inner polymeric layer 68 is applied on a first, tapered, mandrel 96. A second mandrel 97 is inserted into the lumen 72 of the inner polymeric layer 68 created by the excess portion of the inner polymeric layer 68, as described.

A notched or cut outer polymeric tubular layer, such as high density polyethylene tubing that has been notched or cut longitudinally, can be slid onto the tapered mandrel and a portion of the inner liner, starting at the distal end of the tapered mandrel (step 204). The second mandrel can then be removed (step 206). FIG. 32G illustrates a perspective view of the sheath at steps 204 and 206 of FIG. 31. A polymeric outer tubular layer 70 having a longitudinal cut is applied over the tapered mandrel 96 and inner polymeric layer 68. The outer tubular layer conforms to the portion of the inner polymeric layer around the tapered mandrel 96, and the portion of the inner polymeric layer 68 around the second mandrel 97 extends through the longitudinal cut in the outer polymeric tubular layer 70.

A split tool can be inserted into the portion of the lumen of the inner liner that was previously occupied by the second mandrel (step 208). The split tool can then be used to form folds and/or pleats in the excess portion of the inner liner which now extends through the longitudinal cut in the outer polymeric tubular layer (step 210). A radiopaque marker band can optionally be applied at the distal end of the sheath (step 212). Heat shrink tubing, such as FEP heat shrink tubing, can be applied over the entire sheath, and heat can be applied to compress the components of the sheath and bond or fuse them together (step 214). The split tool, heat shrink tubing, and second mandrel can then be removed (step 216). The sheath can then be utilized with a delivery apparatus, such as by bonding the proximal end of the sheath to a polycarbonate housing of a delivery apparatus or catheter assembly (step 218).

FIG. 32H illustrates an elevation view of the sheath at step 218 of FIG. 31. The sheath 66, made according to described methods and processes, can be attached or bonded to a housing 101, such as by bonding the proximal end of the sheath 66 to the polycarbonate housing 101.

In another example, disclosed expandable sheaths can be made using a reflowed mandrel process. A mandrel can be provided, with the size of the mandrel defining the inner diameter of the sheath lumen in its resting configuration. A tube of material, such as a PTFE tube that will become the sheath's inner liner, can be provided with an inner diameter greater than that of the mandrel (e.g., a 9 mm PTFE tube can be mounted on a 6 mm mandrel). The PTFE tube can be mounted on the mandrel and prepared into the final folded configuration by folding the excess material of the PTFE tube over to one or both sides. An HDPE tube that will serve as the outer layer can then be placed over the PTFE liner. The two layer assembly can then be thermally fused together. For example, a reflow process can be performed where the assembly is heated to a temperature high enough such that the inner and/or outer layers are at least partially melted and are then fused together as the heat is removed and the assembly cools.

An elastic cover can be placed over at least part of the fused layers (e.g., over a proximal section of the sheath) and held in place using a thermal process. In some embodiments, the same thermal process can bond the layers of the sheath and the elastic cover. In other embodiments, a first thermal process can be used to fuse the layers of the sheath, and a second thermal process can be used to secure the elastic cover to the sheath. In some embodiments, the elastic cover can be heat shrink tubing that is applied over the expandable sheath, and heated to a temperature high enough to cause the tubing to shrink around the sheath. In some embodiments, a distal soft tip can then be attached to the shaft of the expandable sheath.

In some embodiments, the outer layer can be co-extruded with an adhesive layer, such as a layer formed from Tecoflex, such that the Tecoflex is positioned on an inner surface of the outer layer—in this manner the Tecoflex will be positioned between the inner and outer layers in the completed sheath. In these embodiments, an HDPE tube can be provided with a coating of Tecoflex on the inner surface. The HDPE tube can be slit along the length of the tube to open and flatten it, and then cut using a template in some embodiments. For example, for specific applications, portions of the outer layer can be cut and removed using a template. The cut HDPE can then be placed on the inner layer on the mandrel. In some embodiments, only a portion of the outer layer will have the adhesive Tecoflex. In these embodiments, the sections without Tecoflex will only be partially fused to the inner layer. In some embodiments, the entire inner surface of the outer layer will have the Tecoflex, and the inner surface of the outer layer can be positioned so that it contacts the inner layer on the mandrel. To position the inner and outer layers as shown in the sheath of FIG. 39, the folded portion of the inner layer can be lifted up, and an edge of the outer layer can be tucked beneath the fold.

Sheaths of the present disclosure can be used with various methods of introducing a prosthetic device into a patient's vasculature. One such method comprises positioning an expandable sheath in a patient's vessel, passing a device through the introducer sheath, which causes a portion of the sheath surrounding the device to expand and accommodate the profile of the device, and automatically retracting the expanded portion of the sheath to its original size after the device has passed through the expanded portion. In some methods, the expandable sheath can be sutured to the patient's skin at the insertion site so that once the sheath is inserted the proper distance within the patient's vasculature, it does not move once the implantable device starts to travel through the sheath.

Disclosed embodiments of an expandable sheath can be used with other delivery and minimally invasive surgical components, such as an introducer and loader. In one embodiment, the expandable sheath can be flushed to purge any air within the sheath, using, for example, flush port 103 (FIG. 35). An introducer can be inserted into the expandable sheath and the introducer/sheath combination can be fully inserted into vasculature over a guiding device, such as a 0.35" guidewire. Preferably, the seam formed by the intersection of the folded portion of the inner layer and the overlapping portion of the outer layer can be positioned such it is oriented downward (posterior). Once the sheath and introducer are fully inserted into a patient's vasculature, in some embodiments, the expandable sheath can be sutured in place at the insertion site. In this manner, the expandable sheath can be substantially prevented from moving once positioned within the patient.

The introducer can then be removed and a medical device, such as a transcatheter heart valve can be inserted into the sheath, in some instances using a loader. Such methods can additionally comprise placing the tissue heart valve in a crimped state on the distal end portion of an elongated delivery apparatus, and inserting the elongated delivery device with the crimped valve into and through the expandable sheath. Next, the delivery apparatus can be advanced through the patient's vasculature to the treatment site, where the valve can be implanted.

Typically, the medical device has a greater outer diameter than the diameter of the sheath in its original configuration. The medical device can be advanced through the expandable sheath towards the implantation site, and the expandable sheath can locally expand to accommodate the medical device as the device passes through. The radial force exerted by the medical device can be sufficient to locally expand the sheath to an expanded diameter (e.g., the expanded configuration) just in the area where the medical device is currently located. Once the medical device passes a particular location of the sheath, the sheath can at least partially contract to the smaller diameter of its original configuration. The expandable sheath can thus be expanded without the use of inflatable balloons or other dilators. Once the medical device is implanted, the sheath and any sutures holding in place can be removed. In some embodiments, it is preferable to remove the sheath without rotating it.

In view of the many possible embodiments to which the principles of the disclosed invention can be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A sheath for introducing a prosthetic device into a body, comprising:
a continuous inner layer defining a lumen therethrough, the inner layer having at least one folded portion; and
a discontinuous outer layer having an overlapping portion and an underlying portion, wherein the outer layer is configured so that the overlapping portion overlaps the underlying portion, wherein at least a portion of the folded portion of the inner tubular layer is positioned between the overlapping and underlying portions, and wherein at least a portion of the sheath is configured to expand to accommodate the prosthetic device;
wherein the sheath defines a longitudinal axis and a distal opening at the terminal distal end of the sheath, the distal opening facing in an axial direction extending along the longitudinal axis such that the prosthetic device can be advanced through the lumen and outwardly through the distal opening in the axial direction into the body;
wherein the at least a portion of the sheath is configured such that the sheath locally expands from a rest configuration in which the lumen has a first diameter to an expanded configuration in which the lumen has a second diameter that is larger than the first diameter due to an outwardly directed radial force exerted by the prosthetic device against the inner layer, and then locally contracts at least partially back to the rest configuration as the prosthetic device passes through the lumen.

2. The sheath of claim 1, wherein local expansion of the sheath causes a length of the folded portion to at least partially unfold.

3. The sheath of claim 2, wherein local expansion of the sheath causes a length of the overlapping portion to move circumferentially with respect to the underlying portion.

4. The sheath of claim 1, wherein the inner layer comprises PTFE and the outer layer comprises HDPE and/or Tecoflex.

5. The sheath of claim 4, wherein the inner and outer layers are thermally fused together.

6. The sheath of claim 1, wherein the inner layer comprises a woven fabric and/or braided filaments.

7. The sheath of claim 6, wherein the inner layer comprises yarn filaments of PTFE, PET, PEEK, and/or nylon.

8. The sheath of claim 1, further comprising an elastic outer cover disposed on an external surface of the outer layer.

9. The sheath of claim 8, wherein the elastic outer cover comprises PEBAX, polyurethane, silicone, or polyisoprene.

10. The sheath of claim 1, further comprising a radiopaque marker or filler.

11. The sheath of claim 10, wherein the radiopaque marker or filler comprises a discontinuous band positioned between the inner and outer layers near a distal end of the sheath or embedded within the inner or outer layer.

12. The sheath of claim 1, further comprising a tip portion secured to a distal end of the sheath.

13. The sheath of claim 12, wherein the tip portion is radially expandable.

14. The sheath of claim 13, wherein the tip portion comprises an axially extending score line that splits when the prosthetic device passes through the tip portion.

15. The sheath of claim 1, wherein the outer and inner layers are configured such that when the sheath is in the rest configuration, the lumen has a circular cross-sectional profile defining the first diameter, and when the sheath is in the expanded configuration, the lumen has a circular cross-sectional profile defining the second diameter.

16. A sheath for introducing a prosthetic device into a body, comprising:
 a continuous inner layer defining a lumen therethrough, the inner layer having at least one folded portion; and
 a discontinuous outer layer having an overlapping portion and an underlying portion, wherein the outer layer is configured so that the overlapping portion overlaps the underlying portion, wherein at least a portion of the folded portion of the inner tubular layer is positioned between the overlapping and underlying portions, and wherein at least a portion of the sheath is configured to expand to accommodate the prosthetic device;
 wherein the sheath defines a distal opening at the distal end of the sheath such that the prosthetic device can be advanced through the lumen and outwardly through the distal opening into the body;
 wherein the at least a portion of the sheath is configured such that the sheath locally expands from a rest configuration in which the lumen has a first diameter to an expanded configuration in which the lumen has a second diameter that is larger than the first diameter due to an outwardly directed radial force exerted by the prosthetic device against the inner layer, and then locally contracts at least partially back to the rest configuration as the prosthetic device passes through the lumen;
 wherein the inner layer comprises a circumferential portion having a substantially circular cross-sectional profile, the circumferential portion defining a longitudinally extending seam, the folded portion comprises a first fold portion and a second fold portion, the first and second fold portions extending radially outwardly from respective portions of the circumferential portion on opposite sides of the seam when the sheath is in the rest configuration.

17. The sheath of claim 16, wherein the first fold portion is secured to an inner surface of the overlapping portion of the outer layer and when the sheath is in the rest configuration, an inner surface of the second fold portion contacts an outer surface of the underlying portion of the outer layer and an outer surface of the second fold portion contacts an inner surface of the first fold portion.

18. A method of inserting a prosthetic device into a blood vessel of a patient, the method comprising:
 providing the sheath of claim 1;
 inserting the sheath at least partially into the blood vessel of the patient;
 advancing a prosthetic device through the lumen of the sheath so as to cause the sheath to locally expand from the rest configuration to the expanded configuration from the outwardly directed radially force of the prosthetic device exerted against the inner layer, and then locally contract at least partially back to the rest configuration as the prosthetic device passes through the lumen;
 wherein when the sheath is in the rest configuration, the overlapping portion overlaps the underlying portion with the folded portion of the inner layer disposed between the overlapping portion and the underlying portion.

19. The method of claim 18, wherein the lumen is cylindrical in the rest configuration and the expanded configuration.

* * * * *